(12) United States Patent
Malnoy et al.

(10) Patent No.: US 11,441,157 B2
(45) Date of Patent: Sep. 13, 2022

(54) VITIS VINIFERA WITH REDUCED MLO6 AND MLO11 EXPRESSION AND INCREASED RESISTANCE TO POWDERY MILDEW

(71) Applicant: Fondazione Edmund Mach, San Michele all'Adige (IT)

(72) Inventors: Mickael Malnoy, San Michele all'Adige (IT); Stefano Pessina, Monza (IT); Riccardo Velasco, Nogaredo (IT); Michele Perazzolli, Cles (IT); Luisa Lenzi, Tassullo (IT)

(73) Assignee: Fondazione Edmund Mach, San Michele all'Adige (IT)

( * ) Notice: Subject to any disclaimer, the term of this patent is extended or adjusted under 35 U.S.C. 154(b) by 111 days.

(21) Appl. No.: 16/887,412

(22) Filed: May 29, 2020

(65) Prior Publication Data
US 2020/0291421 A1 Sep. 17, 2020

Related U.S. Application Data

(62) Division of application No. 15/742,147, filed as application No. PCT/EP2016/065860 on Jul. 5, 2016, now Pat. No. 10,683,516.

(30) Foreign Application Priority Data

Jul. 8, 2015 (WO) ................ PCT/EP2015/065624

(51) Int. Cl.
*C12N 15/82* (2006.01)
*A01H 1/00* (2006.01)
*A01H 6/88* (2018.01)

(52) U.S. Cl.
CPC ....... *C12N 15/8282* (2013.01); *A01H 1/1255* (2021.01); *A01H 6/88* (2018.05); *C12N 15/8218* (2013.01)

(58) Field of Classification Search
None
See application file for complete search history.

(56) References Cited

U.S. PATENT DOCUMENTS

| 10,683,516 B2* | 6/2020 | Malnoy ................ C07K 14/415 |
| 2010/0192254 A1 | 7/2010 | Markus et al. |

FOREIGN PATENT DOCUMENTS

| CN | 102719446 A | 10/2012 |
| WO | 9804586 A2 | 2/1998 |
| WO | 2012116938 A1 | 9/2012 |
| WO | 2014062989 A2 | 4/2014 |

OTHER PUBLICATIONS

Winterhagen et al. Transcriptional Up-Regulation of grapevine MLO genes in response to powdery mildew infection.(2008) Am. J. Enol. Vitic.; vol. 59; pp. 159-168 (Year: 2008).*

Mejlhede et al. EcoTILLING for the identification of allelic variation in the powdery mildew resistance genes mlo and Mla of barley. (2006) Plant Breeding; vol. 125; pp. 461-467 (Year: 2006).*

Acevedo-Garcia et al., Magical mystery tour: MLO proteins in plant immunity and beyond, New Phytologist, 2014, vol. 204, pp. 273-281.

Aist et al., Invasion of Plants by Powdery Mildew Fungi, and Cellular Mechanisms of Resistance.

Angeli et al., Is the mycoparasitic activity of Ampelomyces quisqualis biocontrol strains related to phylogeny and hydrolytic enzyme production?, Biological Control, Sep. 23, 2012, vol. 63, pp. 348-358.

Bai et al., Naturally Occuring Borad-Spectrum Powdery Mildew Resistance in a Central American Tomato Accession is Caused by Loss of Mlo Function, Molecular Plant-Microbe Interactions, 2008, vol. 21, No. 1, pp. 30-31.

Bari et al., Role of plant hormones in plant defence responses, Plant Mol Biol, 2009, vol. 69, pp. 473-488.

Baudoin et al., Qoi Resistance of Plasmopara Viticola and Erysiphe necator in the Mid-Atlantic United States, Plant Health Progress, Feb. 11, 2008.

Blaich et al., Studies on conidial germination and initial growth of the grapevine powdery mildew Uncinula necator on artificial substrates, Applied Microbiology and Biotechnology, 1989, vol. 30, pp. 415-421.

Bruce et al., Plant defence signalling induced by biotic attacks, Current Opinion in Plant Biology, 2007, vol. 10, pp. 387-392.

Buschges et al., The Barley Mio Gene: A Novel Control Element of Plant Pathogen Resistance, Cell, Mar. 7, 1997, vol. 88, pp. 695-705.

Calonnec et al., Effects of Unicinula necator on the yield and quality of grapes (*Vitis vinifera*) and wine, Plant Pathology, 2004, vol. 53, pp. 434-445.

Campbell et al., Introduction to Plant Disease Epidemiology, A Wiley-Interscience Publication.

Chen et al., Two Seven-Transmembrane Domain Mildew Resistance Locus O Proteins Confunction in *Arabidopsis* Root Thigmomorphogenesis, The Plant Cell, Jul. 2009, vol. 21, pp. 1972-1991.

Chowdhury et al., Differential accumulation of callose, arabinoxylan and cellulose in nonpenetrated versus penetrated papillae on leaves of barley infected with *Blumeria graminis* f. sp. *hordei*, New Phytologist, Jul. 7, 2014, vol. 204, pp. 650-660.

Collins et al., SNARE-protein-medicated disease resistance at the plant cell wall, Nature, Oct. 30, 2013, vol. 425, Nature Publishing Group.

Consonni et al., Conserved requirement for a plant host cell protein in powdery mildew pathogenesis, Nature Genetics, Jun. 2006, vol. 38, No. 6.

(Continued)

*Primary Examiner* — Cathy Kingdon Worley
(74) *Attorney, Agent, or Firm* — The Webb Law Firm

(57) ABSTRACT

Provided herein are *Vitis vinifera* exhibiting *Erysiphe necator* resistance. In particular, provided herein are *Vitis vinifera* having in their genome mildew resistance locus O (MLO) genes, in particular and MLO6 gene and an MLO11 gene, where the MLO6 gene and MLO11 gene have reduced expression and/or function.

8 Claims, 5 Drawing Sheets

Specification includes a Sequence Listing.

(56) References Cited

OTHER PUBLICATIONS

Costa et al., Development of analytical tools for evaluating the effect of T-DNA chimeric integration on transgene expression in vegetatively propagated plants, Plant Cell Tiss Organ Cult, May 8, 2014, vol. 118, pp. 471-484.
Database EMBL, "vitis vinifera (wiune grape unknown" retrieved from EBI accession No. EMBL CBI31482, Nov. 25, 2009.
Database EMBL, MLO-like protein, retrieved from EBI accession No. EMBL: UNIPROT:D7TMB5, Aug. 10, 2010.
Devoto et al., Topology Subcellular Localization, and Sequence Diversity of the Mlo Family in Plants, The Journal of Biological Chemistry, Dec. 3, 1999, vol. 274, No. 49, p. 34993-35004.
Dufour et al., Assessment of fungicide resistance and pathogen diversity in Erysiphe necator using quantitative real-time PCR assays, Pest Manag Sci, 2011, vol. 67, pp. 60-69.
Dufour et al., Benzothiadiazole-primed defence responses and enhanced differential expression of defence genes in Vitis vinifera infected with biotropic pathogens Erysiphe necator and Plasmopara viticola. Plant Pathology, 2013, vol. 32, pp. 370-382.
Eppo, Guidelines for the biological evaluation of fungicides: Uncinula necator, EPPO Bulletin, 1988, vol. 18, No. 4, pp. 605-612.
Feechan et al., Genetic Dissection of a TIR-NB-LRR locus from the wild North American grapevine species *Muscadinia rotundifolia* identifies paralogous genes conferring resistance to major fungal and oomycete pathogens in cultivated grapevine, The Plant Journal, 2013, vol. 76, pp. 661-674.
Feechan et al., Host Cell Entry of Powdery Mildew is Correlated with Endosomal Transport of Antagonistically Acting VvPEN1 and VvMLO to the Papilla, Molecular Plant-Microbe Interactions, 2013, vol. 26, No. 10, pp. 1138-1150.
Feechan et al., Identification of grapevine MLO gene candidates involved in susceptibility to powdery mildew, Functional Plant Biology, 2008, vol. 35, pp. 1255-1266.
Feechan et al., Mechanisms of powdery mildew resistance in the Vitaceae family, Molecular Plant Pathology, 2011, vol. 12, No. 3, pp. 263-274.
Fuller et al., The value of powdery mildew resistance in grapes: Evidence from California, Wine Economics and Policy, 2014, vol. 3, pp. 90-107.
Fung et al., Powdery Mildew Induces Defense-Oriented Reprogramming of the Transciptome in a Susceptible But Not in a Resistant Grapevine, Plant Physiology, Jan. 2008, vol. 146, pp. 236-249.
Gadoury et al., Ontogenc Resistance to Powdery Mildew in Grape Berries, Phytopathology, vol. 93, No. 5, pp. 547-555.
Gao et al., Down-regulation of acetolactate synthase compromises Ol-1-mediated resistance to powdery mildew in tomato, BMC Plant Biology, 2014, vol. 14, No. 32.
Gao et al., Functions of EDS11-like and PAD4 genes in grapevine defenses against powdery mildew, Plant Mol Biol, 2014, vol. 86, pp. 381-393.
Guo et al., Evolution and expression analysis of the grape (*Vitis vinifera* L.) WRKY gene family, Journal of Experimental Botany, 2014, vol. 65, No. 6, pp. 1513-1528.
Hellemans et al., qBase relative quantification framework and software for management and automated analysis for real-time quantitative PCR data, Genome Biology, Feb. 9, 2007, vol. 8, No. 19.
Huckelhoven, The effective papilla hypothesis, New Phytologist, 2014, vol. 204, pp. 438-440.
Jorgensen, Discovery, characterization and exploitation of Mlo powdery mildew resistance in barley, 1992, Euphytica, vol. 63, pp. 141-152.
Karimi et al., Gateway vectors for Agrobacterium-mediated plant transformation, Trends in Plant Science, May 2002, vol. 7, No. 5.
Kessler et al., Conserved Molecular Components for Pollen Tube Reception and Fungal Invasion, Science, Nov. 12, 2010, vol. 330.

Ling et al., Robust RT-qPCR Data Normalization: Validation and Selection of Internal Reference Genes during Post-Experimental Data Analysis, PLoS One, Mar. 2011, vol. 6:3.
Lorek, Molecular characterization of mlo-based powdery mildew resistance and the role of heterotrimeric G-Protein signaling in *Arabidopsis* defense, 2012.
Lyngkaer et al., The Barley mlo-gene: an important powdery mildew resistance source, Agronomie, 2000, vol. 20, pp. 745-756.
Madden et al., Spatial Aspects of Epidemics-III: Patterns of Plant Disease, The Study of Plant Disease Epidemics, 2007.
Miklis et al., Barley MLO Modulates Actin-Dependent and Actin-Independent Antifungal Defense Pathways at the Cell Periphery, Plant Physiology, Jun. 2007, vol. 144.
Muthmann, The use of plant protection products in the European Union, Eurostat Statistical Books, 2007.
Panstruga, Serpentine plant MLO proteins as entry portals for powdery mildew fungi, Plant Signalling from Genes to Biochemistry, 2005.
Parlevliet, What is Durable Resistance, A General Outline, Durability of disease resistance, 1993, pp. 23-39.
Pavan et al., Loss of susceptibility as a novel breeding strategy for durable and broad-spectrum resistance, Mol Breeding, 2010, vol. 25. pp. 1-12.
Pavan et al., Pea powdery mildew er1 resistance is associated to loss-of-function mutations at a MLO homologous locus, Theor Appl Gene, 2011, vol. 123, pp. 1425-1431.
Pessina et al., Characterization of the MLO gene family in Rosaceae and gene expression analysis in *Malus domestica*, BMC Genomics, 2014, vol. 15, No. 618.
Piffanelli et al., The Barley MLO Modulator of Defense and Cell Death Is Responsive to Biotic and Abiotic Stress Stimuli, Plant Physiology, 2002, vol. 129, pp. 1076-1085.
Pike et al., Members of the NPF3 Transporter Subfamily Encode Pathogen-Inducible Nitrate/Nitrite Transporters in Grapevine and *Arabidopsis*, Plant Cell Physiology, 2014, vol. 55:1, pp. 162-170.
Preuss et al., Targeted Gene Silencing in Plants Using RNA Interference, RNA Interference (RNAi) ~ Nuts & Bolts of siRNA Technology, 2003, pp. 23-36, DNA Press, LLC.
Reid et al., An optimized grapevine RNA isolation procedure and statistical determination of reference genes for real-time RT-PCR during berry development, BMC Plant Biology, 2006, vol. 6, No. 27.
Reinstadler et al., Novel induced mlo mutant alleles in combination with site-directed mutagenesis reveal functionally important domains in the heptahelical barley Mlo protein, BMC Plant Biology, 2010, vol. 10, No. 31.
Robert-Seilaniantz et al., Pathological hormone imbalances, Current Opinion in Plant Biology, 2007, vol. 10, pp. 372-379.
Schweizer et al., Double-stranded RNA interferes with gene function at the single-cell level in cereals. The Plant Journal, 2000, vol. 24, No. 6, pp. 895-903.
Stolzenburg et al., The role of papillae in resistance to powdery mildew conditioned by the ml-o gene in barley. I Correlative evidence, Physiological Plant Pathology, 1984, vol. 25, pp. 337-346.
Strube et al., Evaluation of reference genes for quantitative real-time PCR to investigate protein disulfide isomerase transcription pattern in the bovine lungwarm *Dictyocaulus viviparus*. Gene, 2008, vol. 425, pp. 36-43.
Urso et al., An Agrobacterium tumefaciens-mediated gene silencing system for functional analysis in grapevine, Plant Cell Tiss Organ Cult, 2013, vol. 114, pp. 49-60.
Van Hiel et al., Identification and validation of housekeeping genes in brains of the desert locust *Schistocerca gregaria* under different developmental conditions. BMC Molecular Biology, 2009, vol. 10, No. 56.
Vanacker et al., Eady H2O2 Accumulation in Mesophyll Cells Leads to Induction of Glutathione during the Hypersensitive Response in the Barley-Powdery Mildew Interaction, Plant Physiology, Aug. 2000, vol. 123, pp. 1289-1300.
Ward et al., Coordinate Gene Activity in Response to Agents That Induce Systemic Acquired Resistance, The Plant Cell. Oct. 1991, vol. 3, pp. 1085-1094.

(56) References Cited

OTHER PUBLICATIONS

Wightwick et al., Environmental Risks of Fungicides Used in Horticultural Production Systems, Fungicides, Dec. 14, 2010.
Wilcox, Grapevine Powdery Mildew, 2003.
Winterhagen et al., Transciptional Up-Regulation of Grapevine MLO genes in response to Powdery Mildew Infection, American Society for Enology and Viticulture, 2008, vol. 59, No. 2.
Zhao et al., Efficient RNAi-based gene family knockdown via set cover optimization, Artificial Intelligence in Medicine, 2005, vol. 35, pp. 61-73.
Zheng et al., Loss of Function in Mlo Orthologs Reduces Susceptibility of Pepper and Tomato to Powdery Mildew Disease Caused by Leveillula taurica, Plos One, Jul. 2013, vol. 8:7.
Zottini et al., Agroinfiltration of grapevine leaves for fast transient assays of gene expression and for long-term production of stable transformed cells, Plant Cell Rep, 2008, vol. 27, pp. 845-853.
Calonnec et al., Evaluation of grapevine resistance to downy and powdery mildew in a population segregating for run1 and rpv1 resistance genes, Integrated Protection in Viticulture—IOBC/wprs Bulletin, 2008, vol. 36, pp. 45-52.
Endo et al., Multigene knockout using off-target mutations of the CRISPR/Cas9 system in rice, Plant and Cell Physiology, 2015, vol. 56, pp. 41-47.
Jaillon et al., Unnamed protein product, partial [Vitis vinifera]. (2010) GenBank Accession CBI31482.3; pp. 1-2 (Year: 2010).
Mejlhede et al., EcoTILLING for the identification of allelic variation in the powdery mildew resistance genes mlo and Mloa of barley, Plant Breeding, 2006, vol. 125, pp. 461-467.
Riaz et al., Identification of mildew resistance in wild and cultivated Central Asian grape germplasm, BMC Plant Biology, 2013, vol. 13, pp. 1-21.
The French-Italian Public Consortim for Grapevine Characterization, The grapevine genome sequence suggests ancestral hexaploidization in major angiosperm phyla, Nature, 2007, vol. 449, pp. 463-468.

\* cited by examiner

VITIS VINIFERA WITH REDUCED MLO6 AND MLO11 EXPRESSION AND INCREASED RESISTANCE TO POWDERY MILDEW

CROSS-REFERENCE TO RELATED APPLICATIONS

This application is a divisional of U.S. patent application No. 15/742,147, filed Jan. 5, 2018, now U.S. Pat. No. 10,683,516, which is the United States national phase of International Application No. PCT/EP2016/065860 filed Jul. 5, 2016, and claims priority to International Application No. PCT/EP2015/065624 filed Jul. 8, 2015, the disclosures of which are hereby incorporated in their entirety by reference.

The Sequence Listing associated with this application is filed in electronic format via EFS-Web and is hereby incorporated by reference into the specification in its entirety. The name of the text file containing the Sequence Listing is 1710860_ST25.txt. The size of the text file is 31,621 bytes, and the text file was created on Dec. 27, 2017.

DESCRIPTION

The present invention relates to *Erysiphe necator* resistance conferring genes, plants, plant parts and seeds comprising the present resistance providing genes and the use thereof for selecting *Erysiphe necator* resistant plants.

*Erysiphe necator*, also designated as Uncinula necator, is a fungus causing powdery mildew disease symptoms in grape. The fungus is a common pathogen for *Vitis* species of which the most important species is *Vitis vinifera* or grapevine.

Grapevine requires a huge amount of pesticides, particularly fungicides, to prevent yield losses. Between 1992 and 2003, 73% of the fungicides sold in France, Italy, Spain and Germany, were used for grapevine protection, a crop that covers only 8% of the land used for agriculture in the considered countries (EUROSTAT, 2007).

Grapevine powdery mildew (PM) caused by the fungus *Erysiphe necator*, is one of the most economically relevant diseases of grapevine worldwide. *E. necator* is an obligate biotroph that can infect all green tissues of grapevine and causes significant losses in yield and berry quality. PM symptoms are a white or grey powder covering of the upper and lower surfaces of the leaves. Fruit infections result in shriveling or cracking of the berries. The quality of the fruit is severely damaged, with increased acidity and decreased anthocyanin and sugar content.

Powdery mildew is controlled with frequent applications of chemical fungicides. However, the intense application of chemical fungicides has several drawbacks. First of all, the effects on environment of fungicides are well documented. Secondly, the costs of the chemicals and their applications can reach up to 20% of the total expenses for grape production in some areas. Thirdly, the development of resistant populations of the pathogen was already documented by Baudoin et al. (2008) and Dufour et al. (2011), strongly reducing the efficacy of chemical treatments. Therefore, there is increasing interest in the development of new alternative methods to chemical treatments.

The generation of PM-resistant varieties is one of the best options to make sustainable grapevine cultivation a realistic possibility, preserving at the same time the incomes of the growers. A study carried out on "Chardonnay" production in California, showed that the use of PM-resistant variety could save to the growers around 720 $/ha, with a significant reduction of fungicide usage (Fuller et al., 2014).

Most cultivars of the European grapevine (*Vitis vinifera*), which includes the world's finest and most widely planted wine and table grapevine cultivars, are highly susceptible to PM (Gadoury et al. 2003). In contrast, North American *Vitis* species co-evolved with *E. necator* and possess various level of resistance to the pathogen (Fung et al., 2008). This resistance could be introgressed by crossing *V. vinifera* with one of the resistant American *Vitis* species, but breeding is a slow process in grapevine and the acceptance of resistant hybrids by producers and consumers has been limited in the past (Fuller et al., 2014). The use of technologies like genetic transformation or high-throughput marker-assisted selection can be used to obtain resistant grapevine cultivars with desirable grape properties for producers and consumers (Feechan et al., 2013a).

The most common strategy to develop resistant plants is focused on the introgression of resistance genes (R-genes). R-genes encode proteins that recognize pathogen effectors and trigger defense response, mediated by a signaling network in which plant hormones play a major role (Pavan et al., 2010). Resistance is manifested as localized hypersensitive response at the site of infection (Bari and Jones, 2009). Resistance conferred by R-genes is scarcely durable, as mutations of pathogen effectors, allow it to overcome resistance (Parlevliet et al., 1993).

An alternative approach is based on the inactivation of susceptibility genes (S-genes), defined as genes whose loss-of-function results in recessively inherited resistance (Pavan et al., 2010). Some pathogens are able to suppress plant defense by activating plant proteins which function is the negative regulation of plant immunity system. The genes encoding these plant proteins are known as susceptibility genes (S-genes) and their knock-out release the suppression of plant defense and lead to resistance (Pavan et al., 2010). The disadvantage of S-genes is the pleiotropic phenotypes sometimes associated to their knock-out (Pavan et al. 2011). Mildew Locus O (MLO) genes are a typical example of PM S-genes.

Resistance due to the knock-out of an MLO gene (mlo resistance) was discovered in barley in 1992 (Jorgensen, 1992) and for a long time was considered as a unique form of resistance. However, further studies revealed that MLO genes are largely conserved across plant kingdom and their loss-of-function resulted in resistance in several species, such as *Arabidopsis* (Consonni et al., 2006), pea (Pavan et al., 2011), tomato (Bai et al., 2008) and pepper (Zheng et al., 2013). Not all MLO genes are S-genes and MLO family members are divided in seven clades (Acevedo-Garcia et al., 2014; Pessina et al., 2014). Only two clades contain S-genes: clade IV contains all monocots S-genes (Panstruga et al., 2005; Reinstadler et al., 2010); and clade V contains all dicots S-genes (Consonni et al., 2006; Bai et al., 2008; Feechan et al., 2008; Winterhagen et al., 2008). Not all the members of clades IV and V are S-genes.

Considering the economic impact of an *Erysiphe necator* infection on grape production, there is a continuing need in the art for *Erysiphe necator* resistance providing genes.

It is an object of the present invention, amongst other objects, to meet this need of the art.

SUMMARY OF THE INVENTION

According to the present invention, the above object, amongst other objects is met by providing impaired *Erysiphe necator* resistance providing genes as outlined in the appended claims.

Specifically, the above object, amongst other objects, is met according to a first aspect of the present invention by providing *Erysiphe necator* resistance conferring genes, wherein the amino acid sequence encoded by the resistance conferring gene is the primary amino acid sequence represented by SEQ ID No. 1, or a primary amino acid sequence with more than 70% identity, preferably more than 80% identity, more preferably more than 90% identity, and most preferably more than 95% identity with SEQ ID No. 1 under the condition that the present resistance conferring genes are impaired.

In the alternative, the above object, amongst other objects, is met according to a first aspect of the present invention by providing *Erysiphe necator* resistance conferring genes, wherein the amino acid sequence encoded by the resistance conferring gene is the primary amino acid sequence represented by SEQ ID No. 2, or a primary amino acid sequence with more than 70% identity, preferably more than 80% identity, more preferably more than 90% identity, and most preferably more than 95% identity with SEQ ID No. 2 under the condition that the present resistance conferring genes are impaired.

As yet another alternative, the above object, amongst other objects, is met according to a first aspect of the present invention by providing *Erysiphe necator* resistance conferring genes, wherein the amino acid sequence encoded by the resistance conferring gene is the primary amino acid sequence represented by SEQ ID No. 3, or a primary amino acid sequence with more than 70% identity, preferably more than 80% identity, more preferably more than 90% identity, and most preferably more than 95% identity with SEQ ID No. 3 under the condition that the present resistance conferring genes are impaired.

Sequence identity as used herein is defined as the number of identical consecutive aligned nucleotides, or amino acids, over the full length of the present sequences divided by the number of nucleotides, or amino acids, of the full length of the present sequences and multiplied by 100%. For example, a sequence with 80% identity to SEQ ID No. 1 comprises over the total length of 539 amino acids of SEQ ID No. 1, 431 or 432 identical aligned amino acids, i.e., 430 or 431/539*100%=80%.

An impaired resistance conferring gene according to the present invention is meant to indicate a gene providing a reduced, or even absent, susceptibility to *Erysiphe necator* as indicated by powder-like spots on the leaves and stems.

Impaired resistance conferring genes according to the present invention are mutated genes. The mutation, or mutations, in the present genes can results/result in impairment by different mechanisms. For example, one or more mutations in protein encoding DNA sequences can result in mutated, truncated or non-functional proteins. One or more mutations in non-coding DNA sequences can cause alternative splicing, translation or protein trafficking. Alternatively, one or more mutations resulting in an altered transcriptional activity of a gene, which determines the amount of mRNA available for translation to protein, can result in a resistance due to a low level, or complete absence, of encoded proteins. Additionally, the impairment of the present genes may be caused after translation, i.e. at protein level.

Impaired is also indicated herein as encoding a non-functional gene or protein. Although the function of the present genes is not yet identified, a non-functional gene or protein can be readily determined by establishing *Erysiphe necator* resistance (non-functional) or *Erysiphe necator* susceptibility (functional) in a plant. An *Erysiphe necator* resistance (non-functional) plant is indicated by comprising a gene which is mutated at the protein level as compared to the SEQ ID Nos. 1 or 2 or 3 or reduced levels are observed of mRNA comprising SEQ ID Nos. 4 or 5 or 6.

Functional and non-functional genes, or proteins, can also be determined using complementation experiments. For example, transforming an *Erysiphe necator* resistant *Vitis vinifera* plant with a copy the present genes under the control a constitutive promoter will result in an *Erysiphe necator* susceptible *Vitis vinifera* plant.

According to the present invention, the present *Erysiphe necator* resistance conferring genes provide *Erysiphe necator* resistance when impaired. Impaired according to the present invention can be indicated by the absence, or decrease of a protein identified herein by SEQ ID Nos. 1 or 2 or 3. In the art, many mechanisms are known resulting in the impairment of a gene either at the transcription, translation or protein level.

For example, impairment at the transcription level can be the result of one or more mutations in transcription regulation sequences, such as promoters, enhancers, initiation, termination or intron splicing sequences. These sequences are generally located 5' of, 3' of, or within the coding sequences represented by SEQ ID Nos. 4 and 5 and 6. Impairment can also be provided by a deletion of, rearrangement of or insertion in the present genes.

Impairment at the translation level can be provided by a premature stop-codons or other RNA to protein controlling mechanisms or post-translational modifications influencing, for example, protein folding or cellular trafficking.

Impairment at the protein level can be provided by truncated, misfolded or disturbed protein-protein interactions.

Independent of the underlying mechanism, impairment according to the present invention is indicated by a decrease, or absence, a functional protein according to SEQ ID Nos. 1 or 2 or 3.

Considering the above, according to an embodiment of the first aspect of the present invention, impairment according to the present invention comprises one or more mutations in the present genes resulting in the absence of a protein expression product with a primary amino acid sequence represented by SEQ ID No. 1 or an mRNA comprising SEQ ID No. 4; or, in the alternative the absence of a protein expression product with the primary amino acid sequence represented by SEQ ID No. 2 or 3 or an mRNA comprising SEQ ID No. 5 or 6, respectively.

According to another embodiment of this first aspect of the present invention, the present impairment comprises one or more mutations in the present genes resulting in a non-functional protein expression product.

According to still another embodiment of this first aspect of the present invention, the present impairment comprises a reduced transcription level resulting in a reduced level of an mRNA comprising SEQ ID No. 4 or SEQ ID No. 5 or SEQ ID No. 6.

According to yet another embodiment of this first aspect of the present invention, the present impairment comprises a reduced translation level of an mRNA comprising SEQ ID No. 4 or SEQ ID No. 5 or SEQ ID No. 6.

According to an especially preferred embodiment of the invention, the present *Erysiphe necator* resistance conferring gene is derived from *Vitis vinifera*.

According to a second aspect, the present invention relates to *Vitis vinifera* plants comprising in their genome an impaired *Erysiphe necator* resistance conferring gene as described above wherein the impairment provides *Erysiphe necator* resistance.

According to a preferred embodiment of this second aspect of the present invention, the present *Vitis vinifera* plants show an expression, or transcription, of the present *Erysiphe necator* resistance conferring genes being reduced by at least 10% as compared to a *Vitis vinifera* plant susceptible to *Erysiphe necator*, preferably wherein the expression, or transcription is reduced by at least 20% as compared to a *Vitis vinifera* plant susceptible to *Erysiphe necator*, preferably at least 30%, more preferably at least 50%, even more preferably at least 70%, and most preferably at least 80% such as 25%, 35%, 40%, 45%, 55%, 60%, 65% or 75%.

According to another preferred embodiment of this second aspect of the present invention, the present *Vitis vinifera* plants display an absent expression, or transcription of the present *Erysiphe necator* resistance conferring genes.

According to an especially preferred embodiment of this second aspect of the present invention, the present *Vitis vinifera* plants comprise in their genome an impaired *Erysiphe* necator resistance conferring gene encoding a protein with the primary amino acid sequence of SEQ ID No. 1, or a primary amino acid sequence with more than 70% identity, preferably more than 80% identity, more preferably more than 90% identity, and most preferably more than 95% identity with SEQ ID No. 1; and, in addition, an impaired *Erysiphe necator* resistance conferring gene encoding a protein with the primary amino acid sequence of SEQ ID No. 2, or a primary amino acid sequence with more than 70% identity, preferably more than 80% identity, more preferably more than 90% identity, and most preferably more than 95% identity with SEQ ID No. 2; and/or an impaired *Erysiphe necator* resistance conferring gene encoding a protein with the primary amino acid sequence of SEQ ID No. 3, or a primary amino acid sequence with more than 70% identity, preferably more than 80% identity, more preferably more than 90% identity, and most preferably more than 95% identity with SEQ ID No. 3. Formulated differently, the present invention relates according to an especially preferred embodiment to *Vitis vinifera* plants comprising an impaired VvMLO7 gene in combination with an impaired VvMLO6 or VvMLO11 gene or comprising an impaired VvMLO7 gene in combination with impaired VvMLO6 and VvMLO11 genes.

According to a third aspect, the present invention relates to seeds, plant parts or propagation material of the present *Erysiphe necator* resistant plants comprising in their genome the present one or two impaired *Erysiphe necator* resistance conferring genes providing *Erysiphe* necator resistance.

According to a fourth aspect, the present invention relates to isolated nucleotide sequences represented by SEQ ID Nos. 4 or 5 or 6, or nucleotide sequences with more than 70% identity, preferably more than 80% identity, more preferably more than 90% identity, and most preferably more than 95% identity therewith.

According to a fifth aspect, the present invention relates to isolated amino acid sequences represented by SEQ ID No. 1 or 2 or 3, or amino acid sequences with more than 70% identity, preferably more than 80% identity, more preferably more than 90% identity, and most preferably more than 95% identity therewith.

According to a sixth aspect, the present invention relates to the use of the present *Erysiphe necator* resistance conferring genes, the present isolated nucleotide sequences or the present isolated amino acid sequences for selecting an *Erysiphe necator* resistant *Vitis vinifera* plants using, for example, the present sequences for developing molecular markers.

The present invention will be further detailed in the following example of an especially preferred embodiment of the present invention. In the example, reference is made to figures wherein:

DESCRIPTION OF THE INVENTION

Example

Materials and Methods

Constructs for Grapevine Transformation

Figure 1:
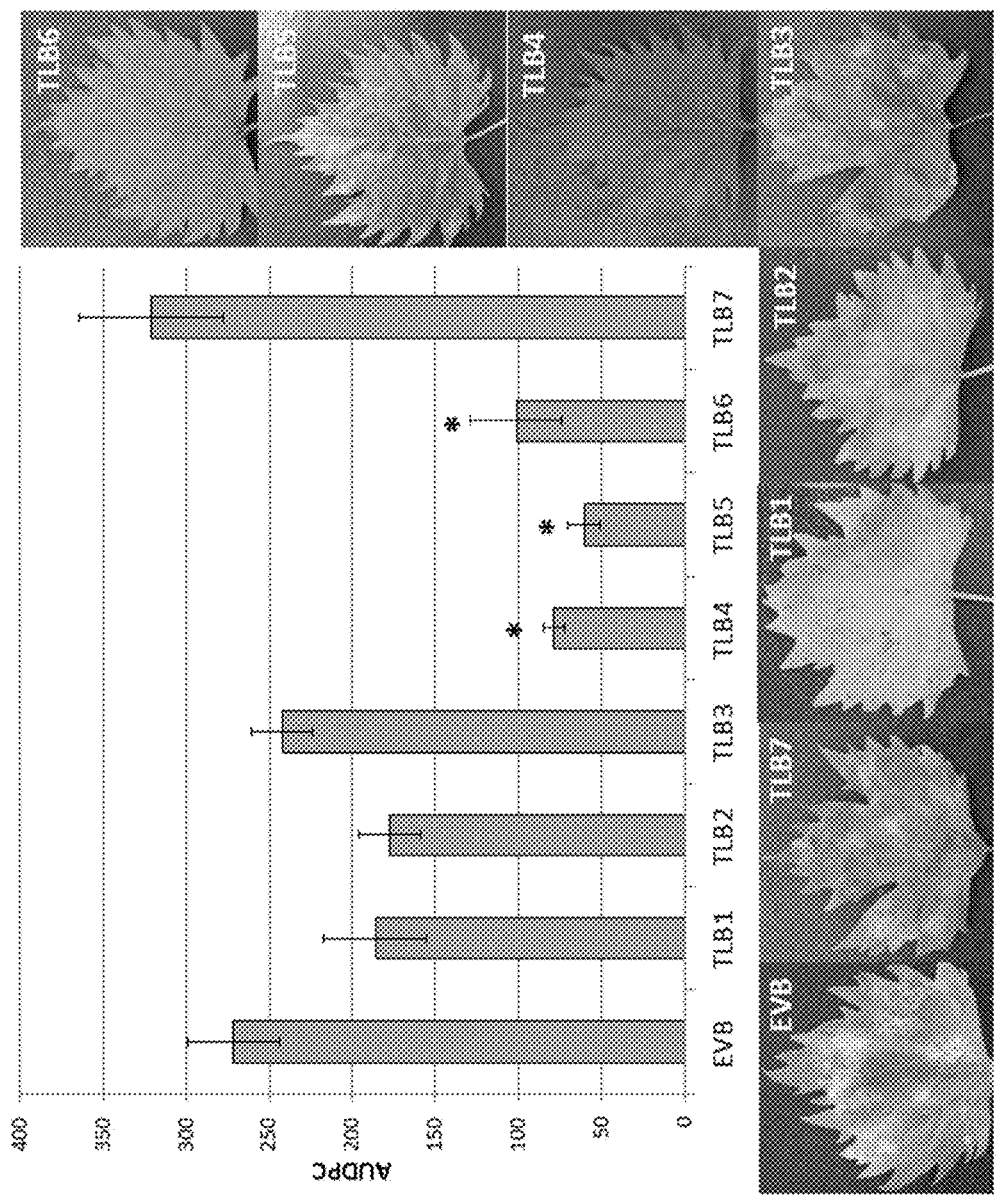
FIG. 1: shows the area under disease progress curve (AUDPC) of grapevines inoculated with *Erysiphe necator* in control (EVB) and transgenic lines (TLB1, TLB2, TLB3, TLB4, TLB5, TLB6 and TLB7). The mean scores of AUDPC values calculated on 8-19 biological replicates from two experiments are reported. Error bars show standard error of the mean. The asterisks indicates statistically significant differences respect to the control line EVB, according to Tukey or Games-Howell post-hoc tests (P=0.05). Pictures of representative leaves for each line were collected 30 days after inoculation.

Fragments of 300-600 bp for the four MLO target genes VvMLO6, VvMLO7, VvMLO11 and VvMLO13 were amplified with specific primer pairs (Table 1) and cloned into the vector pENTR/SD-TOPO (Invitrogen).

TABLE 1

Primers used to amplify MLO genes fragments for the RNAi constructs.

| Gene# | Primer Forward | Primer Reverse |
|---|---|---|
| VvMLO6 | CACCTGCTTACAGT ATTACAAACTCCC (SEQ ID NO: 46) | TTTCCCTTGCA TACCTAAAC (SEQ ID NO: 47) |
| VvMLO7 | CACCGACAATTTT TAACGAGAGAGT (SEQ ID NO: 48) | ATCTCATGTTG GGTTCGGATT (SEQ ID NO: 49) |
| VvMLO11 | CACCTCACTTATG CTACTGGGGTT (SEQ ID NO: 50) | ATCAACTTTGGGA ACTGATCTGAC (SEQ ID NO: 51) |
| VvMLO13 | CACCGAGCTAATG TTGCTAGGGTT (SEQ ID NO: 52) | AAATTTTGCAT GGCTTTGAG (SEQ ID NO: 53) |

After sequence validation, the four gene fragments were cloned in the RNAi Gateway vector pK7GWIWG2D(II) (Karimi et al. 2002) using the procedure described by Urso et al. (2013). The final constructs were verified by sequencing on both strands and were cloned into *Agrobacterium tumefaciens* strain GV3101, as described by Zottini et al. (2008). *A. tumefaciens*-transformed cells were tested by PCR (GoTaq Green Master Mix—Promega, Fitchburg, USA) to confirm the presence of the constructs using specific primers designed to anneal on the 35S promoter (5'-CGCACAATCCCACTATCCTT-3') (SEQ ID NO: 45) and the MLO fragment (Table 1).

Plant Material and Transformation

For grapevine transformation, somatic embryos of *V. vinifera* cultivar Long-Cluster Brachetto were used. The plant material was in vitro cultivated in the darkness in a growth chamber at 20-24° C. and 70±5% relative humidity (RH). Plant transformation, regeneration and selection of the transgenic plants were carried out as described by Dalla Costa et al. (2014). A total of five transformations were performed: four aimed to silence the four MLO target genes, one with an empty vector (pK2WG7), as control.

Screening of Regenerants and Propagation of In Vitro Materials

Genomic DNA was extracted from in vitro leaf tissue using Illustra Nucleon Phytopure kit (GE Healthcare, Buckinghamshire, UK). Transgene integration was evaluated with the same primers used to confirm the presence of the construct in *A. tumefaciens*. The in vitro lines that were confirmed to have the insertion of the transgene were moved to a woody plant (WP) medium (McCown and Lloyd, 1981), kept in growth chamber (20-24° C., 70±5% RH) and transferred in fresh media once a month.

Greenhouse Acclimation

Plants were acclimated to greenhouse conditions with a progressive process carried out in a growth chamber (25° C., 16 hours day/8 hours night, humidity 70±5%). One-month old-plants with a well-developed root apparatus (at least two main roots, 3 cm long) were transferred in a 250 ml plastic cup containing wet autoclaved turf (Terriccio Vegetal Radic—Tercomposti Spa, Brescia, Italy) and sealed with parafilm, to preserve humidity. Every seven days, one or two holes were made in the parafilm layer, to progressively reduce the humidity of the environment and promote the formation of the foliar cuticle. After three weeks, the parafilm sealing was completely removed and, after one week, plants were transferred into 1 L pots and grown under greenhouse conditions (25° C., 16 hours day/8 hours night, humidity 70±5%).

*Erysiphe necator* Inoculation and Disease Severity Assessment

The PM inoculum was obtained from infected leaves of an untreated vineyard in northern Italy (Trentino region) and maintained by subsequent inoculations on *V. vinifera* "Pinot Noir" plants under greenhouse conditions. The plants were dry inoculated with PM by gentle brushing from infected young leaves carrying freshly sporulation *E. necator* onto the target leaves (Blaich et al., 1989). Inoculated plants were incubated in the greenhouse at 25° C. with a relative humidity (RH) of 100% for 6 h to promote the fungal penetration into the leaves, and then maintained at 25° C. with a relative humidity of 70±10% until the last symptom's evaluation. Disease severity was visually assessed on all leaves at 14, 22 and 30 days post inoculation (dpi), according to the standard guidelines of the European and Mediterranean Plant Protection Organisation (EPPO, 1998).

Disease severity was expressed as the proportion (percentage of 0 to 100%, with intervals of 5%) of adaxial leaf area covered by PM mycelia in relation to the total leaf area, and a mean value was calculated for each plant. Two inoculation experiments were carried out. For each experiment, three to nine biological replicates (plants) per line were analyzed in a randomized complete block design. The reduction of disease severity was calculated according to the following formula: [(disease severity in control plants–disease severity in treated plants)/disease severity in control plants]×100. To analyze all the time points together, we used the area under disease progress curve (AUDPC), a quantitative summary of disease intensity over time (Campbell and Madden, 1990; Madden et al., 2007).

To evaluate the disease severity, the number of *E. necator* conidia produced from infected leaves was assessed as described by Angeli et al. (2012) with slight modifications. Three leaves were collected from each replicate at 30 dpi and four disks of 0.8 cm diameter for each leaf were cut for a total of 12 disks for replicate. Leaf disks were transferred to 50 mL tubes containing 5 mL distilled water with 0.01% Tween 80 (Sigma-Aldrich, Sant Louis, USA). Tubes were vortexed for one min and the concentration of conidia per ml was determined by counting with a haemocytometer under a light microscope. The amount of conidia was finally converted in conidia per square centimeter ($cm^2$) of grapevine leaf.

Histological Analysis

Two inoculated leaves were collected from three biological replicate of each transgenic and control line at 3, 10 and 21 dpi and subjected to histological analysis. To visualize fungal hyphae, leaves were cleared and stained as described by Vanacker et al. (2000) changed as follow: leaves were cut in small pieces and laid with the adaxial surface up on filter paper moistened with an ethanol:glacial acetic acid mixture (3:1, v/v) until the chlorophyll had been removed. Leaf pieces were transferred to water soaked filter paper for 2 h, then transferred on a microscope slide and a drop of aniline blue (0.1% [w/v] in lactoglycerol) was pipetted onto leaf surface. Hyphae were visualized using the bright field illumination of a Leica LMD6500 microscope (Leica Microsystems, Wetzlar, Germany).

For the detection of papilla, leaves were cleared in an ethanol:glacial acetic acid mixture (3:1, v/v) until the chlorophyll had been removed, and equilibrated overnight in a solution containing lactic acid, glycerol and water (1:1:1). Papillae were visualized using the LMD filter (BP filter 380-420 nm excitation, 415 dichroic mirror, and BP 445-485 nm emission) of a Leica LMD6500 microscope (Leica Microsystem, Wetzlar, Germany).

Sample Collection, RNA Extraction and Gene Expression Analysis

The first gene expression analysis was carried out on in vitro transgenic plants, to identify silenced lines, with three biological replicates collected. For the second analysis, carried out on acclimated transgenic plants, leaf samples were collected immediately before inoculation, 24 hours and 10 days post PM inoculation. These time points were chosen because are associated with the up-regulation of MLO genes during E. necator infection (Feechan et al., 2008; Winterhagen et al., 2008). For each line at each time point, leaf samples were collected from five different plants. Each sample comprised two half leaves taken from the same plant; only leaves of the third and fifth nodes from the top of the shoot were collected. Samples were immediately frozen in liquid nitrogen and stored at 80° C.

Total RNA was extracted with the Spectrum™ Plant Total RNA kit (Sigma-Aldrich), treated with the DNAse I (Sigma-Aldrich) and reverse transcribed using the SuperScript III reverse transcriptase (Invitrogen, Life Technologies, Waltham, USA).

The qPCR analysis was performed with Advanced Universal SYBR Green Supermix (Bio-Rad, Hercules, USA) in a 15-µL reaction volume with specific primers (Table 2), using a CFX96 Touch Real-Time PCR detection system (Bio-Rad, Hercules, USA), run by CFX Manager software.

TABLE 2

Primers used to amplify MLO genes fragments for the qPCR analysis.

| Name | Forward ('5 - '3) | Reverse ('5 - '3) |
| --- | --- | --- |
| EF1α | GAACTGGGTG CTTGATAGGC (SEQ ID NO: 7) | AACCAAAATATC CGGAGTAAAAGA (SEQ ID NO: 8) |
| GAPDH | TTCTCGTTGAG GGCTATTCCA (SEQ ID NO: 9) | CCACAGACTTC ATCGGTGACA (SEQ ID NO: 10) |
| Actin | TCCTTGCCTTG CGTCATCTAT (SEQ ID NO: 11) | CACCAATCACTC TCCTGCTACAA (SEQ ID NO: 12) |
| VvMLO6 | GTGCAGTTATG TGACACTCCC (SEQ ID NO: 13) | ACACACCAT CCGAGTGC (SEQ ID NO: 14) |
| VvMLO7 | CTTTCTTCGC ATGGAGCACG (SEQ ID NO: 15) | GAGCCCATCT GTGTCACCAA (SEQ ID NO: 16) |
| VvMLO11 | GCACCCCCT TACATGGC (SEQ ID NO: 17) | TCTGGACCAGGA TTTCTATGATG (SEQ ID NO: 18) |
| VvMLO13 | CTGGTGACAC AGATGGGTTC (SEQ ID NO: 19) | CTACTTGACA TGGGTGTGGC (SEQ ID NO: 20) |
| VvWRKY19 | GGGGAGGCTG TGGTTAGGTT (SEQ ID NO: 21) | GTTTGGCATT TGGCTTGTCT (SEQ ID NO: 22) |
| VvWRKY27 | CTTGGATCAGA ATCACCCCTAA (SEQ ID NO: 23) | GCCGTGGTATG TGGTTTTGTA (SEQ ID NO: 24) |

TABLE 2-continued

Primers used to amplify MLO genes fragments for the qPCR analysis.

| Name | Forward ('5 - '3) | Reverse ('5 - '3) |
| --- | --- | --- |
| VvWRKY48 | CAAGATTTCAA GGACCAAGCAG (SEQ ID NO: 25) | AGTATGCCTTC CTCGGTATGT (SEQ ID NO: 26) |
| VvWRKY52 | CCTCTTGATGA TGGGTTTAGTT (SEQ ID NO: 27) | GTCTTCCACGG TAGGTGATTT (SEQ ID NO: 28) |
| VvALS1 | CCGTGCATAC CGAGCATTTG (SEQ ID NO: 54) | AGGCCGGTTC TGTATGTTGG (SEQ ID NO: 55) |
| VvEDS1 | AGGGTTTTATATT GTTATCTCAAGGC (SEQ ID NO: 29) | GGAAGAAAATATCTTAT TACTACATAATGTTTC (SEQ ID NO: 30) |
| VvLOX9 | GACAAGAAGG ACGAGCCTTG (SEQ ID NO: 31) | CATAAGGGTA CTGCCCGAAA (SEQ ID NO: 32) |
| VvLOX1 | ATCAATGCTC TTGCTCGGGA (SEQ ID NO: 33) | CCAGAGCTGG TCATAGGCAG (SEQ ID NO: 34) |
| VvPAD4 | ACGATTGCAC TGGTAAGCCA (SEQ ID NO: 35) | CGACTCCGTC ATCGCCTAAA (SEQ ID NO: 36) |
| VvPEN1 | CTTCGCAAGA AGCTCAGGGA (SEQ ID NO: 37) | TGCTCTTGGA TCGCCTTCTG (SEQ ID NO: 38) |
| VvPR1 | CCCAGAACTC TCCACAGGAC (SEQ ID NO: 39) | GCAGCTACAG TGTCGTTCCA (SEQ ID NO: 40) |
| VvPR6 | ACGAAACGG CATCGTAATC (SEQ ID NO: 41) | TCTTACTGGG GCACCATTTC (SEQ ID NO: 42) |
| VvNPF3.2 | TCGTCACATC AGCACAGCTT (SEQ ID NO: 43) | ATCTGCGAGC CAATGGAACA (SEQ ID NO: 44) |

The software applies comparative quantification with an adaptive baseline. Samples were run in two technical replicates with the following thermal cycling parameters: 95° C. 3 min, followed by 40 cycles of 95° C. 10 sec and 55° C. 30 sec with a final step at 95° C. 10 sec. Primers for gene expression analysis of VvMLO6, VvMLO11 and VvMLO13 were taken from Winterhagen et al. (2008), while for VvMLO7 we designed our specific primer pair (Table 2). Expression of marker genes modulated in the interaction between plants and PM were also analyzed. Primers for VvWRKY19, VvWRKY27, VvWRKY48 and VvWRKY52 were taken from Guo et al. (2014), primers for VvEDS1 from Gao et al. (2014) and primers for VvPR1, VvPR6 and VvLOX9 from Dufour et al. (2013). The new primer pairs were designed with the NCBI Primer Designing Tool (Table 2). Four serial dilutions of cDNA (¹⁄₁₀-¹⁄₁₀₀-¹⁄₁₀₀₀-¹⁄₁₀₀₀₀) were used to calculate the efficiency of the primer pairs and the size of the products was confirmed by agarose gel electrophoresis. Presence of a specific final dissociation curve was determined after every qPCR run with progressive increments of temperature from 65° C. to 95° C. (0.5° C. each step, 5 sec).

The reference genes were Elongation Factor 1a (GenBank accession number EC959059), GAPDH (GenBank accession number CB973647) and Actin (GenBank accession number AY6807019), known to be reference for grapevine (Reid et al., 2006). In this work the stability of these genes was confirmed using the software GeNorm (medgen.u-gent.be/Hydesomp/genorm/). All three reference genes had M-values lower than 0.5, when an M-value lower than 1.5 was generally considered as stable enough (Ling and Salvaterra, 2011; Van Hiel et al., 2009; Strube et al., 2008).

The threshold cycles (Ct) were converted to relative expression with the system proposed by Hellemans et al. (2007), using as input the average Ct of two technical replicates. Hellemans method takes into account the efficiency value of each primer pair. As reference Ct, we used the average Ct of all the samples for the expression of MLO genes, whereas for the analysis on other genes involved in plant defense or mlo resistance, we used the control EVB at T=0. The two different methods were selected for graphical reasons.

Statistical Analysis

Disease Severity

Severity data were analyzed using the Statistica 9 software (StatSoft, Tulsa, USA) and the statistical package SPSS (IBM, Armonk, USA). The smallest statistical unit was the whole plant. We averaged the severity values of all the leaves of the plant and used the resulting average severity for further analysis. Data with a normal distribution (Kolmogorov-Smirnov and Shapiro-Wilk tests P>0.05) were validated for variances homogeneity (Levene's test, P>0.05) and subsequently used for one-way ANOVA with Tukey's post-hoc test, to detect significant differences (P<0.05) at each time point. Data were transformed with the following equation y=arcsin(x), in order to meet the pre-requisites of the ANOVA. In case of non-homogeneous variances, the Games-Howell's post-hoc test was used.

Data from the two experiments were pooled, and the analysis carried out independently for the three time points (14, 22 and 30 dpi). AUDPC data were analyzed as described above for severity data. Data of the conidia counts were analyzed with Kruskall-Wallis test (P<0.05).

qPCR Data Analysis

For the gene expression analysis, values of relative expression were transformed in logarithmic scale according to the equation Y=ln(x) (Pessina et al., 2014) to obtain normal distribution and homogeneity of variances of the residues, assessed with the tests of Shapiro-Wilk (P≤0.05) and Levene (P≤0.05), respectively. Pairwise comparison of homoscedastic data was carried out with Tukey's test (P<0.05), whereas non-homoscedastic data were analyzed with Games-Howell test (P<0.05) using the statistical package SPSS (IBM).

The relative expression of MLO genes from two experiments were analyzed independently and subsequently pooled. To assess differences in expression, one-way ANOVA with Tukey post-hoc test (P<0.05) was used to detect significant differences at each time point. In addition, a two-way ANOVA with Tukey post-hoc test (P<0.05) was used on all the data, to consider at the same time the effects of the transgenic line and of the time point. We drew conclusions from this test only when there were no significant interactions (P>0.05) between the factors time point and transgenic line. For the gene expression characterization of TLB4, we used Fisher as post-hoc test.

Correlation

We used the two-tailed Pearson's correlation test to investigate two possible correlations: between disease severity and amount of conidia at 30 dpi and between disease severity at 14 dpi and relative expression of MLO genes at 10 dpi. In both cases, all data, severity and relative expression, have been transformed with the following equation y=arcsin(x), to achieve normal distribution.

Results

Transformation, Selection and Acclimation of MLO Transgenic Lines

A total of five gene transfers were carried out. Four were aimed to knock-down (KD) specific MLO genes (i=KD-VvMLO6, ii=KD-VvMLO7, iii=KD-VvMLO11, iv=KD-VvMLO13), the fifth to insert an empty vector. Thirty-four regenerated lines were obtained, with 26 of them confirmed to contain the insert (Table S3). The result of the PCR analysis of six lines is shown in Fig. S1. Twenty-six transgenic lines were propagated in vitro and tested for the silencing of MLO genes with qPCR. This was evident for three lines out of eight from gene transfer (iii) (KD-VvMLO11), and three out of nine from gene transfer (iv) (KD-VvMLO13). Gene transfers (i) (KD-VvMLO6) and (ii) (KD-VvMLO7) resulted in a small number of regenerated lines that showed no reduction of expression (Table S3). Regenerated lines were also tested for off-target silencing, showing that the RNAi fragments targeted other clade V MLO genes. Six lines with various combinations of silenced genes were selected and indicated with acronims TLB1 (Transgenic Line of Brachetto) to TLB6 (Table S3). Lines from TLB1 to 3 came from gene transfer (iii) (KD-VvMLO11), lines from TLB4 to TLB6 from gene transfer (iv) (KD-VvMLO13) (Table S3). The control was the EVB line (Empty Vector Brachetto). In addition, TLB7, a regenerated line with no reduction of expression, was also considered. All lines, including the control, will be referred in the text as "transgenic lines". Lines from TLB1 to 7 are further indicated as "RNAi lines" and from TLB1 to 6 "mlo lines".

The survival rate of plants to the acclimation process was around 85%. Under greenhouse conditions, the transgenic plants showed normal growth and no pleiotropic phenotypes.

Powdery Mildew Resistance of Transgenic Lines

PM inoculation was carried out on the seven RNAi lines (TLB1, TLB2, TLB3, TLB4, TLB5, TLB6, TLB7), and the transgenic control line EVB in two independent experiments. Three mlo lines, TLB4, TLB5 and TLB6, showed a significant reduction of *E. necator* infection (FIG. 1) which was greater than 60% at 30 dpi (Table 3).

TABLE 3

Disease reduction of seven RNAi lines.

| | Number of plants | Disease reduction %* | | | Average Disease reduction (%) |
|---|---|---|---|---|---|
| | | 14 dpi | 22 dpi | 30 dpi | |
| TLB1 | 8 | 22.8 | 32.3 | 34.3 | 29.8 |
| TLB2 | 15 | 49.2 | 37.2 | 23.8 | 36.8 |
| TLB3 | 15 | 17.9 | 14.8 | 2.0 | 11.6 |
| TLB4 | 19 | 60.8 | 71.7 | 72.8 | 68.4 |
| TLB5 | 14 | 76.7 | 79.1 | 74.0 | 76.6 |
| TLB6 | 11 | 71.8 | 63.1 | 60.3 | 65.1 |
| TLB7 | 13 | −8.0[#] | −21.5[#] | −21.2[#] | −16.9[#] |

*Line EVB was used as control (12 replicates) and disease reduction was calculated as (Disease severity of EVB-disease severity of the transgenic line)/disease severity of EVB × 100.
[#]The negative values of TLB7 mean that the line showed higher level of infection compared to EVB The disease reduction of TLB6 decreased with the progression of the infection (Table 3), possibly because of the secondary infections coming from nearby infected plants.

TLB2, TLB3, and TLB7 showed a level of susceptibility to PM comparable to the EVB control (FIG. 1 and Table 2). The leaves in FIG. 1 showed the differences between resistant and susceptible lines. All the mlo lines showed reduction of conidia on the leaves surface at 30 dpi, and the decrease was statistically significant only for TLB4, TLB5 and TLB6. TLB4 showed a reduction of 93% of conidia, TLB5 of 95% and TLB6 of 72% compared to the EVB plants. The conidia counts and the disease severity were positively correlated (P=0.01), with a Pearson correlation coefficient of 0.578. This means that the reduction of symptoms on the leaves reflected the lower number of conidia on the resistant lines.

Figure 2:
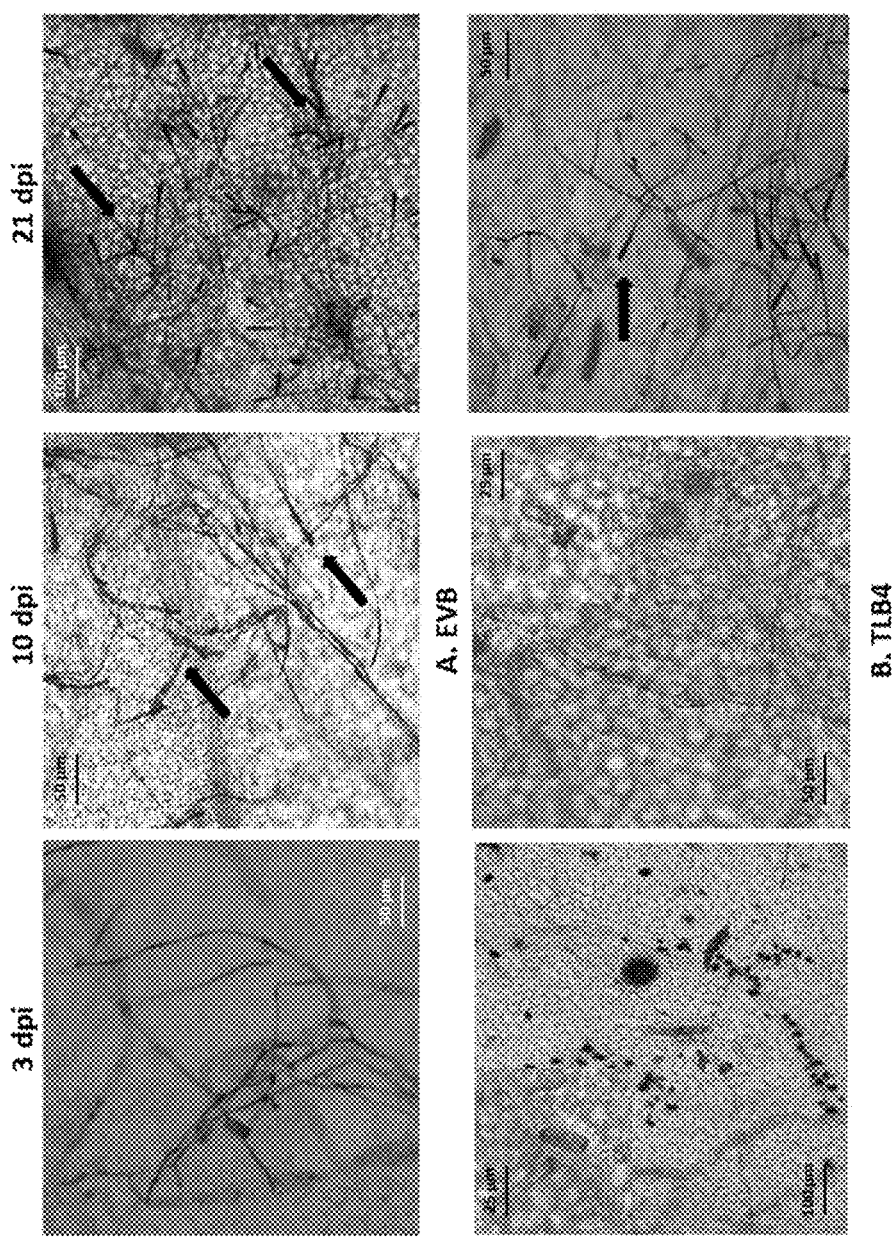
FIG. 2: shows Germination of *Erysiphe necator* conidia in the control line EVB (A) and in the resistant transgenic line TLB4 (B). Microscopy images of infected leaves were taken at 3, 10 and 21 days post inoculation (dpi) with powdery mildew. Insert at high magnification highlighted the germination of an *Erysiphe necator* conidia at 3 dpi and 10 dpi.
Figure 3:
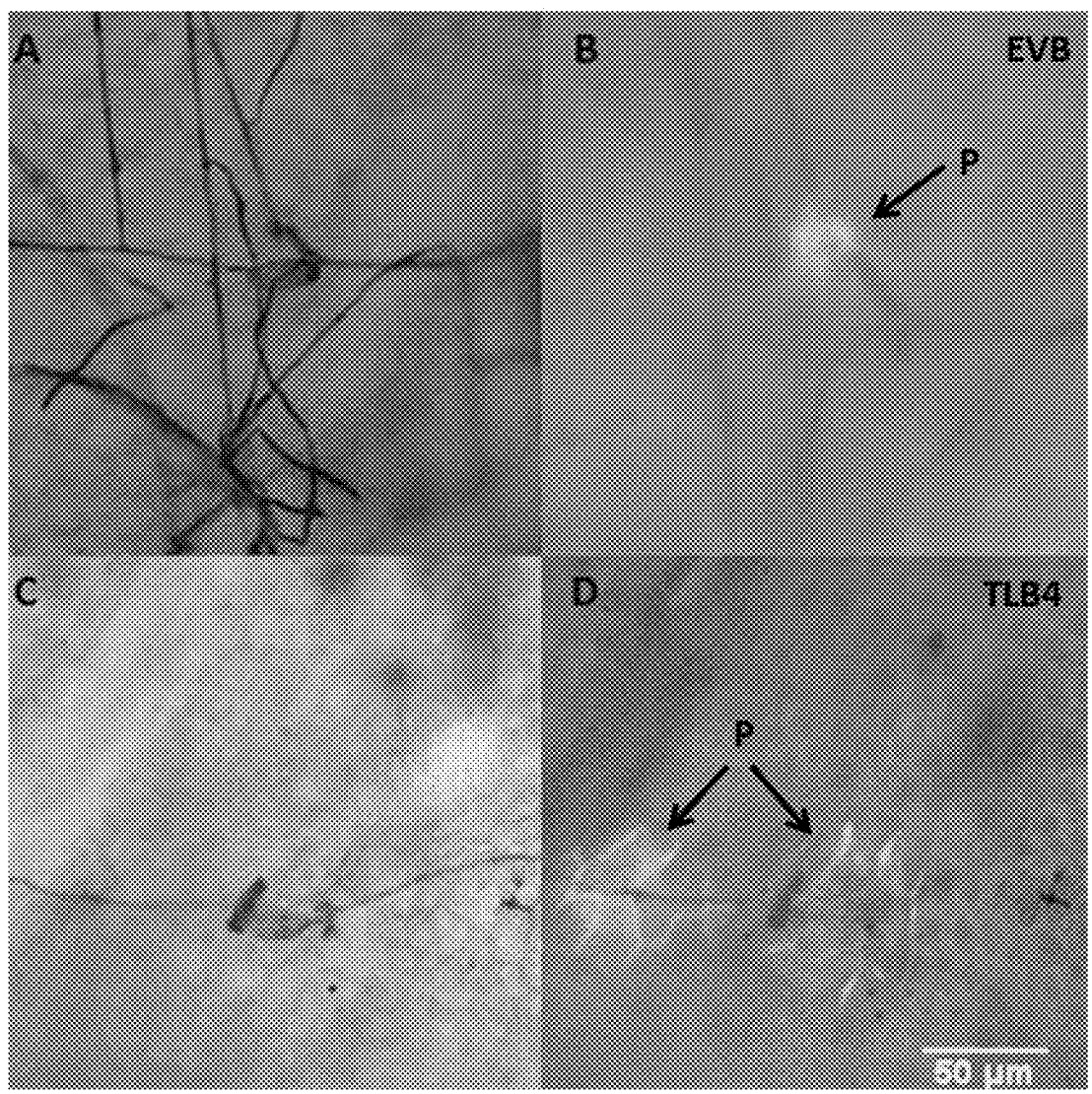
FIG. 3: shows formation of papillae in the control line EVB (A, B) and in the resistant transgenic line TLB4 (C, D). Microscopy images taken with a bright field (A, C) and fluorescence (B, D) microscope at three days post inoculation (dpi). The arrows indicate the papillae (P). The scale bar is the same for the four images.

Line TLB4 was further characterized by histological analysis, demonstrating a reduced progression of PM infection compared to EVB plants at 3 dpi (FIG. 2). In EVB, the first conidiophores appeared at 10 dpi, and at 21 dpi they were spread all over the leaf surface (FIG. 2A). On the other hand, conidiophores were visible only at 21 dpi and in a limited number on TLB4 leaves (FIG. 2B). The formation of papilla was observed in TLB4 and EVB at 3 dpi (FIG. 3). The papilla of EVB had defined edges and it was present only in correspondence of the infection site of *E. necator* (FIG. 3B). Conversely, the papilla detected in TLB4 was more diffuse, bigger and formed in more than one site of infection of the fungus compared to EVB (FIG. 3D).

Figure 4:
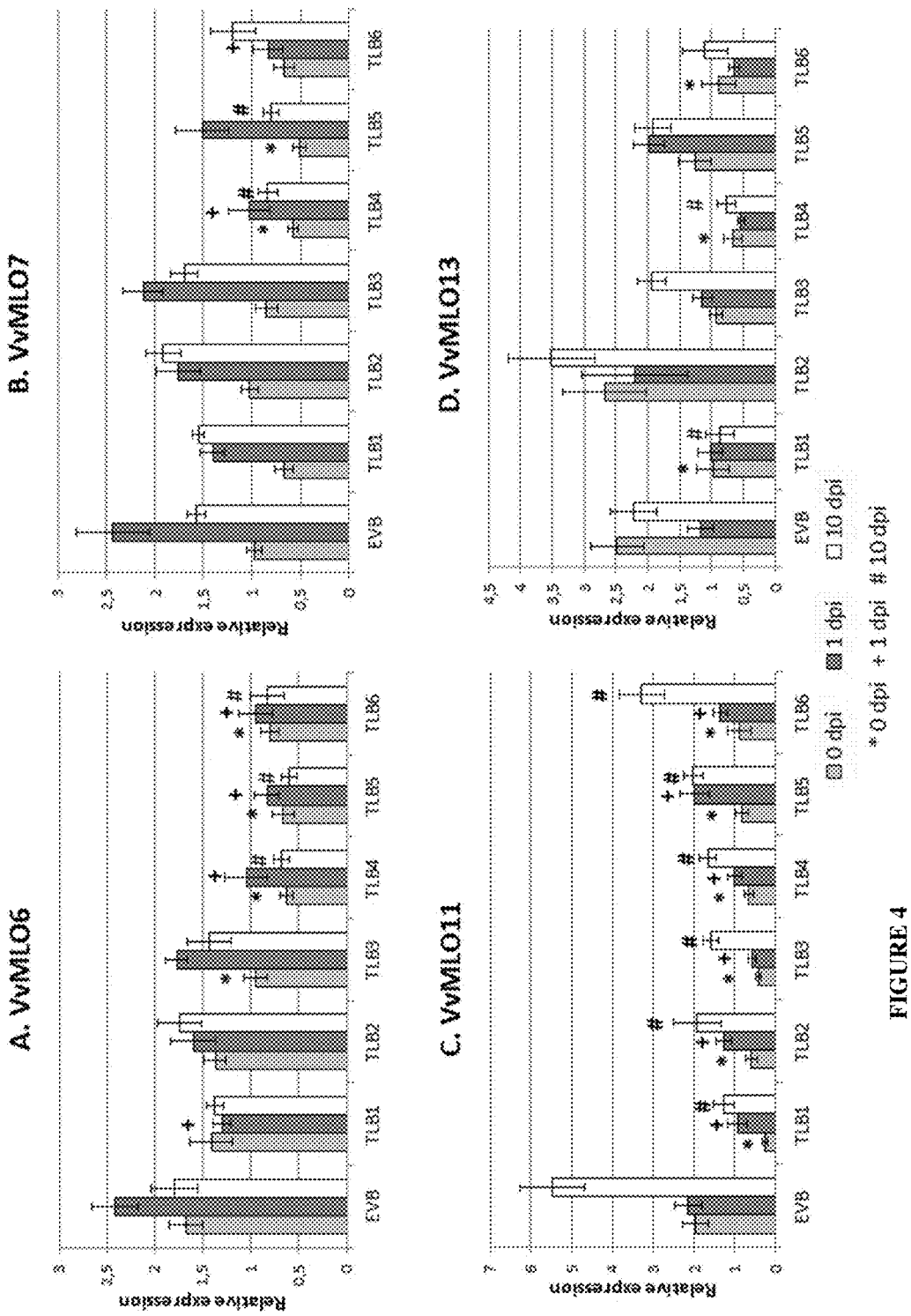
FIG. 4: shows gene expression of four grapevine MLO genes in the six mlo lines (TLB1, TLB2, TLB3, TLB4, TLB5, and TLB6) following inoculation with *Erysiphe* necator. Expression of VvMLO6 (A), VvMLO7 (B), VvMLO11 (C) and VvMLO13 (D) was analyzed before (0 dpi; light grey), one (dark grey), and ten (white) days post inoculation. The mean scores calculated from five to nine plants pooled from the two experiments are reported for each line. Error bars show standard error of the mean. For each time point, symbols highlight significant differences respect to the control EVB, according to Tukey or Games-Howell post-hoc test (P=0.05): * for 0 dpi, + for 1 dpi and # for 10 dpi.

Expression of MLO Genes in the MLO Transgenic Lines and Correlation with Severity Six mlo lines (TLB1, TLB2, TLB3, TLB4, TLB5, TLB6) and the control EVB were examined by gene expression analysis. Gene expression analysis of the four clade V MLO genes in the transgenic lines confirmed the off-target silencing seen in vitro and showed some variability among time points (FIG. 4). Lines TLB1, TLB2 and TLB3, all transformed with the constructe aimed to silence VvMLO11, indeed had the target gene VvMLO11 silenced. TLB1 showed also the silencing of VvMLO13 and TLB3 of VvMLO6 (Table 4).

TABLE 4

Relative expression# of four MLO genes

|  | VvMLO6 | VvMLO7 | VvMLO11 | VvMLO13 |
|---|---|---|---|---|
| TLB1 | 67% | 72% | 25%** | 49%** |
| TLB2 | 79% | 94% | 40%** | 156% |
| TLB3 | 71%* | 93% | 27%** | 69% |
| TLB4 | 38%** | 49%** | 34%** | 33%** |
| TLB5 | 35%** | 55%** | 50%** | 88% |
| TLB6 | 42%** | 53%** | 55%** | 45%** |

Each relative expression (RE %) value is the average of the values of three time points (0 dpi, 1 dpi, 10 dpi) in two experiments. RE % was calculated as follow: RE % = (RE of control EVB/RE of mlo line)*100.
*statistically significant difference at P = 0.05, accordint to Tukey post-hoc test.
**statistically significant difference at P = 0.01, accordint to Tukey post-hoc test.

Lines TLB4, TLB5 and TLB6, coming from the transformation aimed to silence VvMLO13, showed more off-target silencing. In TLB4 and TLB6, all four clade V MLO genes were silenced, whereas In TLB5 VvMLO6, VvMLO7 and VvMLO11 were silenced (Table 4).

A statistically significant (P=0.05) positive Pearson's correlation was found between the relative expression of VvMLO7 and the severity of PM symptoms, but not for the other three MLO genes. The Pearson correlation coefficiency for VvMLO7 was 0.272, meaning that the correlation, although significant, was weak.

Gene Expression Analysis of the mlo Line TLB4

Figure 5:
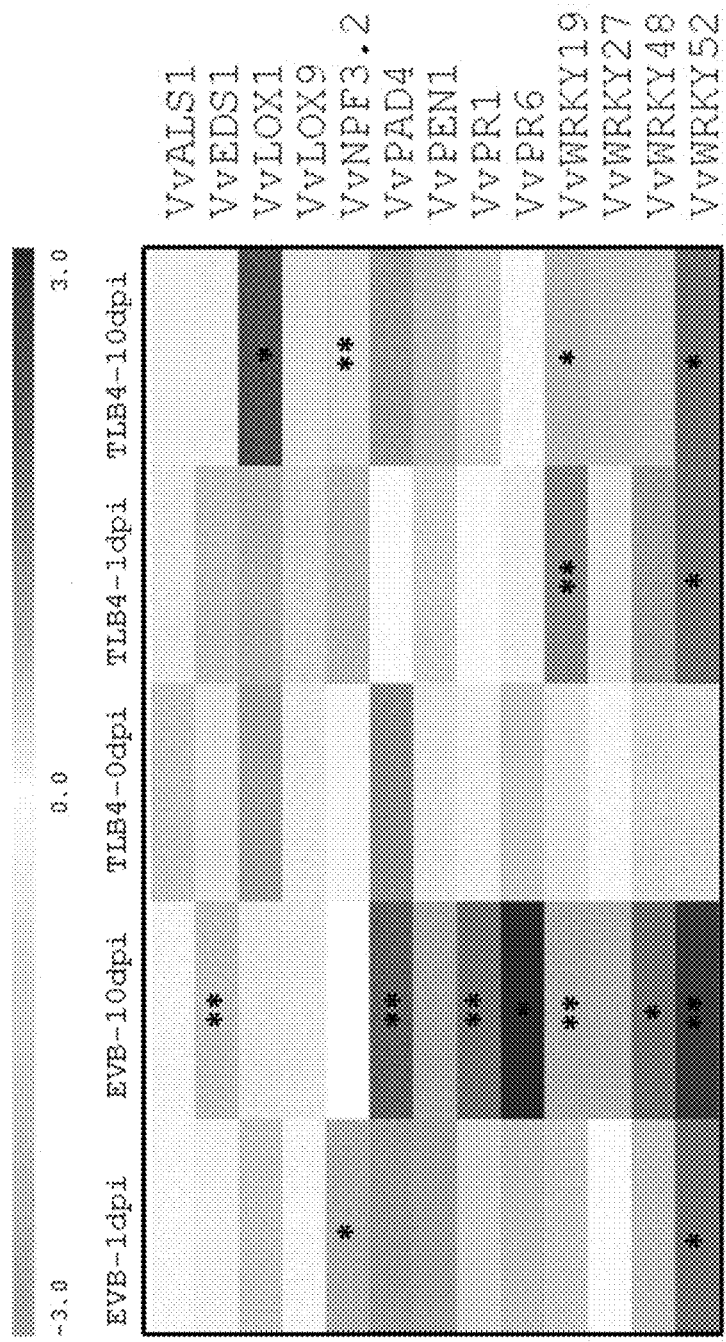
FIG. 5: shows relative expression of 13 grapevine genes at three time points in the control line EVB and in the resistant line TLB4. The color scale indicates the relative expression values calculated respect to the control EVB at 0 dpi, used as reference for data normalization. The asterisks highlight statistically significant differences according to Fisher post-hoc test. One and two asterisks indicate significance at P=0.05 and P=0.01, respectively. The image was prepared with the Multiexperiment Viewer software with the Log 2 of relative expression data

The expression profile of 13 genes known to be modulated following PM infections was carried out on the resistant line TLB4 at three time points (FIG. 5). Line TLB4 was selected because it has all four MLO clade V genes silenced. In EVB, we observed a general up-regulation of genes, especially at 10 dpi. Instead, in the transgenic line TLB4, fewer genes were up-regulated and the intensity of up-regulation, in terms of fold-change, was limited. Moreover, three genes were down-regulated in TLB4 after inoculation, namely VvPR6 (PATHOGENESIS RELATED) at 1 dpi and VvNPF3.2 (NITRATE TRANSPORTER/PEPTIDE TRANSPORTER FAMILY) and VvALS1 (ACETOLACTATE SYNTHASE) at 10 dpi. It is noteworthy that, before the inoculation, there were no differences in expression between TLB4 and the control EVB.

Discussion

Loss-of-function mutations of MLO genes reduce susceptibility to PM in barley (Buschges et al., 1997), *Arabidopsis* (Consonni et al., 2006), pea (Pavan et al., 2011), tomato (Bai et al., 2008), wheat (Wang et al., 2014), and pepper (Zheng et al., 2013). Because in dicots all Clade V MLO S-genes are implicated in PM susceptibility (Consonni et al., 2006; Bai et al., 2008; Feechan et al., 2008; Winterhagen et al., 2008), the aim of this work was to identify which of the clade V MLO genes of grapevine has a role in PM susceptibility, and can thus be inactivated to develop resistant genotypes. Out of 26 transgenic lines, six from gene transfers (iii) (KD-VvMLO11) and (iv) (KD-VvMLO13) supported significant gene knock-down. In the regenerated lines obtained from gene transfers (i) (KD-VvMLO6) and (ii) (KD-VvMLO7), reduction of expression was not evident. It cannot be excluded that this was due to the short RNAi fragments present in the constructs (Preuss and Pikaard, 2003). The detection of off-target silencing in five of the six mentioned lines was expected, as clade V MLO genes have high levels of sequence identity (36-60%, 46% on average; Feechan et al., 2008; Winterhagen et al., 2008). To find a balance between specificity (short RNAi fragments) and effectiveness (long RNAi fragments) is particularly difficult in gene families with high sequence similarity (Zhao et al., 2005). Since the aim was to study the effect of the knock-down of four MLO genes quite similar to each other, we opted for long RNAi fragments, so that off-target silencing was not only expected, but also desired. Knock-out and knock-down of MLO genes may induce pleiotropic phenotypes, like necrotic spot on leaves and reduced grain yield in barley (Jorgensen, 1992), slow growth in *Arabidopsis* (Consonni et al., 2006) and reduced plant size in pepper (Zheng et al., 2013). In grapevine, no pleiotropic phenotypes were observed under the experimental conditions adopted.

Lines TLB4, 5 and 6, which showed clear resistance to PM, allowed to study the link between resistance and the expression of specific MLO genes. VvMLO11 expression was significantly reduced in susceptible and resistant mlo lines: it is concluded that its knock-down was not directly linked to grapevine susceptibility to PM. VvMLO6 was significantly silenced in the resistant lines TLB4, 5 and 6 and in the susceptible line TLB3. Like for VvMLO11, the knock-down of VvMLO6 in both susceptible and resistant lines indicates that this should not be a S-gene. Similarly to VvMLO6, VvMLO13 was knocked-down in the resistant lines TLB4 and 6, but also in the susceptible line TLB1. VvMLO7 was knocked-down only in the three resistant lines TLB4, 5 and 6; the conclusion is that VvMLO7 represents the main candidate for causing PM susceptibility in *V. vinifera*. The significant positive correlation between the relative expression of VvMLO7 and the disease severity in the MLO transgenic lines, stimulates the conclusion that either site directed mutagenesis or searching for natural non-functional alleles may be used in breeding programs to obtain PM resistant genotypes. It was, however, noted that VvMLO7 was always knocked-down together with other two or three MLO genes. Also in *Arabidopsis* the contemporary knock-out of three MLO genes is necessary to obtain complete resistance: knock-out of AtMLO2 results in a moderate level of resistance, whereas knock-out of AtMLO6 and AtMLO12, alone or combined, does not decrease the intensity of the infection. When AtMLO2 is knocked-out together with AtMLO6 or AtMLO12, the level of resistance rises, to become complete when the three genes are knocked-out together (Consonni et al., 2006). In grapevine, VvMLO7 seemed to act like AtMLO2 of *Arabidopsis*. Two candidates for an additive and synergistic role in PM susceptibility in grapevine are VvMLO6 and VvMLO11, since their expression was significantly reduced in all three resistant lines. In *Arabidopsis*, the knock-out of three MLO genes induces complete resistance (Consonni et al., 2006), a situation not observed in grapevine, in agreement with the incomplete silencing of MLO genes obtained by the RNAi approach. A complementation test, carried out in *Arabidopsis* mlo triple mutant, showed that VvMLO11 and VvMLO13 induce susceptibility to PM, whereas VvMLO7 has only a partial effect and VvMLO6 has no effect at all (Feechan et al., 2013b). However, single and double VvMLO11 and VvMLO13 knock-down mutants of *V. vinifera* obtained by RNAi, did not show significant reduction of PM penetration (Qiu et al., 2015). Accordingly, our data indicated VvMLO7 as the main S-gene of grapevine, with a putative additive effect provided by VvMLO11 and VvMLO6. The role of VvMLO6 would be particularly surprising, as it was not up-regulated during PM infection (Feechan et al., 2008; Winterhagen et al., 2008). Conversely, VvMLO13, which knock-down was expected to provide a significant effect on PM susceptibility, turned out to be ineffective. However, it should be considered that Feechan et al. (2013b) operated in a heterologous system (*Arabidopsis*) not reproducing with fidelity the PM infection of grapevine plants.

The precise mechanism through which the reduction of MLO genes expression ends up in resistance to PM pathogens is not completely clear. Resistance seems linked to secretory vesicles traffic (Millis et al., 2007; Feechan et al., 2011) and to the formation of cell wall appositions called papillae (Consonni et al., 2006). These structures consists of a callose matrix enriched in proteins and autofluorogenic phenolics compounds (Vanacker et al. 2000), and their formation depends on endomembrane transport (Hückel-hoven, 2014). The results shown in this paper indicate that all transgenic lines accumulate autofluorigenic materials overimposed to the papilla structure, although shape and dimensions of papillae were different in resistant and susceptible lines. It is known that the defense response based on papillae differs between resistant and susceptible genotypes in timing of formation, composition and size (Chowdhury et al., 2014; Hückelhoven, 2014; Lyngkjxr et al. 2000). Rapid formation of papillae in mlo resistant barley (Lyngkjær et al. 2000) and increased size (Stolzenburg et al., 1984) correlate with mlo resistance. In grapevine, papilla formation is restricted to the site of infection in control plants, whereas it is diffused in the resistant line TLB4. Chowdhury et al. (2014) showed that the difference between effective and non-effective papillae is due to the higher concentration of callose, cellulose and arabinoxylan of the effective ones.

This suggests that, in the case of grapevine, different types of fluorescence could reflect differences in the composition of the papillae. The MLO protein has been proposed to be a negative regulator of vesicle-associated and actin-dependent defense pathways at the site of attempted PM penetration (Panstruga, 2005). Furthermore, Miklis et al. (2007) proposed that, once MLO proteins are under the control of the fungus, actin filaments serve the purpose of supplying nutrients for the growing hyphae through vesicular transport. It is like if the pathogen is able to control the transport of material to the cell-wall, with the purpose of changing the composition of the papillae and turning them from effective to non-effective.

The formation of papillae is not the only process instigated by the activity of MLO genes. To understand the effect of MLO knock-down on other genes involved in plant-pathogen interaction, the expression of 13 genes known to be differentially expressed after PM inoculation was analyzed. In the resistant line TLB4, the knock-down of MLO genes did not affect the level of expression of the 13 genes in absence of PM infection. Under *E. necator* infection (Guo et al., 2014), transcription factors VvWRKY19, VvWRKY48 and VvWRKY52 are up-regulated: the same genes appeared up-regulated in EVB in our experiments, but they were so at a much lower level in TLB4. VvNPF3.2, a nitrite/nitrate transporter up-regulated in grapevine infected with *E. necator* (Pike et al., 2014), was down-regulated in TLB4 at 10 dpi, indicating that in this line only a severe infection elicits VvNPF3.2 up-regulation. VvEDS1 (enhanced disease susceptibility) and VvPAD4 (phytoalexin deficient) are grapevine defense genes involved in the salicylic acid (SA) pathway (Gao F. et al., 2014). SA activates pathogenesis related genes and induces disease resistance (Ward et al., 1991). Both genes were up-regulated in the control line EVB at 10 dpi (VvPAD4 also at 1 dpi). This may indicate that only a heavy *E. necator* infection triggers the plant defense depending on SA. VvEDS1 was not up-regulated in TLB4, whereas VvPAD4 was up-regulated only at 10 dpi, like if the level of PM infection was insufficient to activate the reaction of the plant. Up-regulation in the control and no up-regulation in TLB4 was also observed for both VvPR1 and VvPR6, pathogenesis-related genes involved in plant defense and known to be up-regulated in PM infected grapevine leaves pre-treated with an SA analogue (Dufour et al., 2013). VvLOX1 encodes a lipoxygenase and is the homologous to *Arabidopsis* AtLOX2, that is up-regulated in plants infected with PM spores (Lorek, 2012). Surprisingly, this gene was up-regulated in TLB4 at 10 dpi, but not in EVB. A second lipoxygenase, VvLOX9, did not show in the grapevine lines considered any change in expression, despite being known to be involved in plant defense (Dufour et al., 2013). VvPEN1 (penetration) encodes for a SNARE protein homologous to *Arabidopsis* AtPEN1 and barley ROR2, which have important roles in PM penetration resistance (Collins et al., 2003). VvPEN1 when expressed in a heterologous system (*Arabidopsis*), is known to co-localize with VvMLO11 at sites of attempted PM penetration (Feechan et al., 20013b). However, infection with *E. necator* did not cause any change of its expression. VvALS1 is the homologous of a tomato acetolactate synthase, a key enzyme in the biosynthesis of the amino acids valine, leucine and isoluecine, and involved in mlo-mediated resistance (Gao D. et al., 2014). Silencing of SlALS1 in mlo tomato compromises its resistance, suggesting that amino acid homeostasis is an important process connected to mlo resistance (Gao D. et al., 2014). The complete lack of transcriptional change indicated that the function of this gene in grapevine does not depend on the transcript level. The knock-out of MLO genes increased susceptibility to other pathogens in barley (Jarosch et al., 1999; Kumar et al., 2001) and *Arabidopsis* (Consonni et al., 2006). The infection with *P. viticola*, an obligate biotroph fungus like *E. necator*, revealed that the knockdown of MLO genes did not change the susceptibility of grapevine to downy mildew, supporting the conclusion that MLOs S-genes are specific for *E. necator* and are not involved in the plant interaction with *P. viticola*.

Conclusions

The knock-down of MLO genes substantially reduces PM susceptibility of *Vitis vinifera*. The reduction of expression of VvMLO7 was the main factor involved in resistance, but the additive effects of VvMLO6 and VvMLO11 knockdown further contribute in reducing PM severity. Absolute resistance was not observed, as expected based on the incomplete silencing of MLO genes via RNAi. In mlo lines, no pleiotropic phenotypes were detected under greenhouse conditions. This work provides a crucial information that can be used in breeding grapevine varieties resistant to *E. necator*. The tagging via genome editing of the MLO genes identified in this paper, particularly of VvMLO7, should results in knock-out mutants highly resistant to PM. Alternatively, the search in *V. vinifera* and in wild species of non-functional MLO alleles, particularly of VvMLO7, should contribute to the creation of durable resistance.

Abbreviations

AUDPC: area under disease progress curve
dpi: days post inoculation
EVB: empty vector Brachetto
PM: powdery mildew
RE: relative expressionSA: salicylic acid
TLB1-7=Transgenic Line Brachetto 1-7

REFERENCES

Acevedo-Garcia J, Kusch S, Panstruga R: *Magical mystery tour: MLO proteins in plant immunity and beyond*. New Phytol 2014, 204(2):273-81
Aist J R, Bushnell W R: *Invasion of plants by powdery mildew fungi, and cellular mechanisms of resistance*. The Fungal Spore and Disease Initiation in Plants and Animals. Edited by Cole G T, Hoch H C. New YorK: plenum press; 1991:321-345.
Angeli D, Puopolo G, Maurhofer M, Gessler C, Pertot I: *Is the mycoparasitic activity of Ampelomyces quisqualis biocontrol strains related to phylogeny and hydrolytic enzyme production?* Biological Control 2012, 63; 348-358
Bai Y, Pavan S, Zheng Z, Zappel N, Reinstadler A, Lotti C, De Giovanni C, Ricciardi L, Lindhout P, Visser R G F, Theres K, Panstruga R: *Naturally occurring broad-spectrum powdery mildew resistance in a Central American tomato accession is caused by loss of MLO function*. MPMI 2008, 21: 30-39
Bari R, Jones J D G: *Role of plant hormones in plant defense responses*. Plant Mol Biol, 2009, 69:473-488.
Baudoin A, Olaya G, Delmotte F, Colcol J F, Sierotzki H: *QoI resistance of Plasmopara viticola and Erysiphe necator in the mid-Atlantic United States*. Plant Health Prog 2008, doi:10.1094/PHP-2008-0211-02-RS.
Blaich R, Heintz C, Wind R: *Studies on conidial germination and initial growth of the grapevine powdery mildew Uncinula necator on artificial substrates*. Appl Microbiology Biotechnology 1989, 30, (4), 415-421
Bruce T J A, Pickett J A: *Plant defense signaling induced by biotic attacks*. Curr Opin Plant Biol 2007, 10:387-392.
Bilschges R, Hollricher K, Panstruga R, Simons G, Wolter M, Frijters A, van Daelen R, van der Lee T, Diergaarde P, Groenendijk J, Topsch S, Vos P, Salamini F, Schulze-Lefert P: *The barley Mlo gene: a novel control element of plant pathogen resistance*. Cell 1997, 88 (5):695-705
Calonnec A, Cartolaro P, Poupot C, Dubourdieu D, Darriet P: *Effects of Uncinula necator on the yield and quality of grapes (Vitis vinifera) and wine*. Plant Pathol 2004, 53(4):434-445.
Campbell C L, Madden L V: *Introduction to Plant Disease Epidemiology*. John Wiley and Sons 1990, New York. 532 pp.
Chen Z, Noir S, Kwaaitaal M, Hartmann A, Wu M J, Mudgil Y, Sukumar P, Muday G, Panstruga R, Jones A M: *Two seven-transmembrane domain MILDEW RESISTANCE LOCUS O proteins cofunction in Arabidopsis root thigmomorphogenesis*. Plant Cell 2009, 21:1972-1991.
Chowdhury J, Henderson M, Schweizer P, Burton R A, Fincher G B, Little A: *Differential accumulation of callose, arabinoxylan and cellulose in nonpenetrated versus penetrated papillae on leaves of barley infected with Blumeria graminis f. sp. Hordei*. New Phytol 2014, 204: 650-660
Collins N C, Thordal-Christensen H, Lipka V, Bau S, Kombrink E, Qiu J L, Huckelhoven R, Stein M, Freialdenhoven A, Somerville S C, Schulze-Lefert P: *SNARE-protein-mediated disease resistance at the plant cell wall*. Nature 2003, 425, 973-977.
Consonni C, Humphry M E, Hartmann H A, Livaja M, Durner J, Westphal L, Vogel J, Lipka V, Kemmerling B, Schulze-Lefert P, Somerville S C, Panstruga R: *Conserved requirement for a plant host cell protein in powdery mildew pathogenesis*. Nature Genetics 2006, 38(6): 716-720.
Dalla Costa L, Pinto-Sintra A L, Campa M, Poletti V, Martinelli L, Malnoy M: *Development of analytical tools for evaluating the effect of T-DNA chimeric integration on transgene expression in vegetatively propagated plants*. Plant Cell Tiss Organ Cult 2014 118:471-484
Devoto A, Piffanelli P, Nilsson I, Wallin E, Panstruga R, Von Heijne G, Schulze-Lefert P: *Topology, subcellular localization, and sequence diversity of the Mlo family in plants*. J Biol Chem 1999, 274:34993-35004
Dufour M C, Fontaine S, Montarry J, Corio-Costet M E: *Assessment of fungicide resistance and pathogen diversity in Erysiphe necator using quantitative real-time PCR assays*. Pest Manag. Sci. 2011, 67, 60-69.
Dufour M C, Lambert C, Bouscaut J, Mérillon J M, Corio-Costet M F: *Benzothiadiazole-primed defence responses and enhanced differential expression of defence genes in Vitis vinifera infected with biotrophic pathogens Erysiphe necator and Plasmopara viticola*. Plant Pathol 2013, 62(2): 370-382
EPPO: *Guideline for the biological evaluation of fungicides: Uncinula necator*. EPPO Bulletin 1998, 18:605-612.
Feechan A, Jermakow A M, Torregrosa L, Panstruga R, Dry I B: *Identification of grapevine MLO gene candidates involved in susceptibility to powdery mildew*. Funct Plant Biol 2008, 35:1255-1266
Feechan A, Kabbara s, Dry I B: *Mechanisms of powdery mildew resistance in the Vitaceae family*. Mol Plant Pathology 2011, 12(3):263-274

Feechan A, Anderson C, Torregrosa L, Jermakow A, Mestre P, Wiedemann-Merdinoglu S, Merdinoglu D, Walker A R, Cadle-Davidson L, Reisch B, Aubourg S, Bentahar N, Shrestha B, Bouquet A, Adam-Blondon A F, Thomas M R, Dry I B: *Genetic dissection of a TIR-NB-LRR locus from the wild North American grapevine species Muscadinia rotundifolia identifies paralogous genes conferring resistance to major fungal and oomycete pathogens in cultivated grapevine. Plant J* 2013a, 76, 661-674

Feechan A, Jermakow A M, Ivancevic A, Godfrey D, Pak H, Panstruga R, Dry I B: *Host cell entry of powdery mildew is correlated with endosomal transport of antagonistically acting VvPEN1 and VvMLO to the papilla. Mol Plant Microbe Interact.* 2013b, 26(10):1138-50.

Fuller K B, Alston J M, Sambucci O: *The Value of Powdery Mildew Resistance in Grapes: Evidence from California. Wine economics and policy* 2014

Fung R W M, Gonzalo M, Fekete C, Kovacs L G, He Y, Marsh E, McIntyre L M, Schachtman D P, Qiu W: *Powdery mildew induces defense-oriented reprogramming of the transcriptome in a susceptible but not in a resistant grapevine. Plant Physiology* 2008, 146: 236-249.

Gadoury D M, Seem R C, Ficke A, Wilcox W F: *Ontogenic Resistance to Powdery Mildew in Grape Berries. Phytopathology* 2003, 93: 5, 547-555

Gao D, Huibers R P, Loonen A E, Visser R G F, Wolters A M, Bai Y: *Down-regulation of acetolactate synthase compromises Ol-1-mediated resistance to powdery mildew in tomato. BMC Plant Biol* 2014, 14:32

Gao F, Dai R, Pike S M, Qiu W, Gassmann W: *Functions of EDS1-like and PAD4 genes in grapevine defenses against powdery mildew. Plant Mol Biol* 2014, 86(4-5):381-93

Guo C, Guo R, Xu X, Gao M, Li X, Song J, Zheng Y and Wang X: *Evolution and expression analysis of the grape (V. vinifera) WRKY gene family. J Exp Bot* 2014, 65(6): 1513-28

Hellemans J, Mortier G, De Paepe A, Speleman F and Vandesompele J: *qBase relative quantification framework and software for management and automated analysis of real-time quantitative PCR data. Genome Biol.* 2007, 8:R19

Hückelhoven R: *The effective papilla hypothesis. New Phytol* 2014, 204: 438-440

Jørgensen J H: *Discovery, characterization and exploitation of Mbo powdery mildew resistance in barley. Euphytica* 1992, 63:141-152.

Karimi M, Inze D, Depicker A: *GATEWAY™ vectors for Agrobacterium-mediated plant transformation. Trends Plant Sci* 2002, 7:193-195

Kessler S A, Shimosato-Asano H, Keinath N F, Wuest S E, Ingram G, Panstruga R, Grossniklaus U: *Conserved molecular components for pollen tube reception and fungal invasion. Science* 2010, 330:968.

Ling D, Salvaterra P M: *Robust R T-qPCR Data Normalization: Validation and Selection of Internal Reference Genes during Post-Experimental Data Analysis. PLOS One* 2011, 6:3

Lyngkjær M F, Newton A C, Atzema J L, Baker S J: *The Barley mlo-gene: an important powdery mildew source.* Agronomie 2000, 20 745-756.

Lorek J A: *Molecular characterization of mlo-based powdery mildew resistance and the role of heterotrimeric G-protein signaling in Arabidopsis defense.* PhD dissertation, Universität zu Köln; 2012.

Madden L V, Hughes G, Van Den Bosch F: *The Study of Plant Disease Epidemics.* APS Press, St. Paul, 2007.

McCown B H, Lloyd G: *Woody plant medium (WPM)—a mineral nutrient formulation for microculture of woody plant species. Hortic Sci* 1981, 16:453

Miklis M, Consonni C, Bhat R A, Lipka V, Schulze-Lefert P, Panstruga R: *Barley MLO modulates actin-dependent and actin-independent antifungal defense pathways at the cell periphery. Plant Physiol* 2007, 144:1132-1143

Muthman R: *The use of plant protection products in the European Union.* Eurostat 2007, ISBN 92-79-03890-7

Panstruga R: *Serpentine plant MLO proteins as entry portals for powdery mildew fungi. Biochem Soc Transact* 2005, 33(Pt 2):389-392

Parlevliet J E: *What is durable resistance, a general outline. In Durability of Disease Resistance.* Edited by Jacobs T H, Parlevliet J E. Dordrecht: Kluwer; 1993:23-29.

Pavan S, Jacobsen E, Visser R G F, Bai Y: *Loss of susceptibility as a novel breeding strategy for durable and broad-spectrum resistance. Mol Breed* 2010, 25:1-12.

Pavan S, Schiavulli A, Appiano M, Marcotrigiano A R, Cillo F, Visser R G F, Bai Y, Lotti C, Ricciardi L: *Pea powdery mildew er1 resistance is associated to loss-of-function mutations at a MLO homologous locus. Theor Appl Gen* 2011, 123:1425-1431

Pessina S, Pavan S, Catalano D, Gallotta A, Visser R G F, Bai Y, Malnoy M, Schouten H J: *Characterization of the MLO gene family in Rosaceae and gene expression analysis in Malus domestica. BMC genomics* 2014, 15:618

Piffanelli P, Zhou F S, Casais C, Orme J, Jarosch B, Schaffrath U, Collins N C, Panstruga R, Schulze-Lefert P: *The barley MLO modulator of defense and cell death is responsive to biotic and abiotic stress stimuli. Plant Physiol* 2002, 129:1076-1085

Pike S, Gao F, Kim M J, Kim S H, Schachtman D P, Gassmann W: *Members of the NPF3 Transporter Subfamily Encode Pathogen-Inducible Nitrate/Nitrite Transporters in Grapevine and Arabidopsis. Plant Cell Physiol* 2014, 55(1):162-70

Preuss S, Pikaard C S: *Targeted gene silencing in plants using RNA interference. RNA Interference (RNAi): Nuts & Bolts of siRNA Technology,* 2003, pp. 23-36.

Reid K E, Olsson N, Schlosser J, Peng F, Lund S T: *An optimized grapevine RNA isolation procedure and statistical determination of reference genes for real-time RT-PCR during berry development. BMC Plant Biol* 2006, 6:27

Reinstadler A, Müller J, Czembor J H, Piffanelli P, Panstruga R: *Novel induced mlo mutant alleles in combination with site-directed mutagenesis reveal functionally important domains in the heptahelical barley Mlo protein.* BMC Plant Biol 2010, 10:31.

Robert-Seilaniantz A, Navarro L, Bari R, Jones J D G: *Pathological hormone imbalances. Curr Opin Plant Biol* 2007, 10:372-379.

Stolzenburg M, Aist J R, Israel H W: *The role of papillae in resistance to powdery mildew conditioned by the ml-o gene in barley. I Correlative evidence Physiological Plant Pathology* 1984, 25, 337-346

Strube C, Buschbaum S, Wolken S, Schnieder T: *Evaluation of reference genes for quantitative real-time PCR to investigate protein disulfide isomerase transcription pattern in the bovine lungworm Dictyocaulus viviparus. Gene* 2008, 425: 36-43

Urso S, Zottini M, Ruberti C, Lo Schiavo F, Stanca A M, Cattivelli L, Vale G: *An Agrobacterium tumefaciens-mediated gene silencing system for functional analysis in grapevine. Plant Cell Tiss Organ Cult* 2013, 114(1): 49-60.

Vanacker H, Carver T L W, Foyer C H: *Early $H_2O_2$ accumulation in mesophyll cells leads to induction of glutathione during hypersensitive response in the barley-powdery mildew interaction. Plant Physiology* 2000, 123: 1289-1300

Van Hiel M B, Van Wielendaele P, Temmerman L, Van Soest S, Vuerinckx K, et al.: *Identification and validation of housekeeping genes in brains of the desert locust Schistocerca gregaria under different developmental conditions. BMC Mol Biol* 2009, 10:56

Ward E R, Uknes S J, Williams S C, Dincher S S, Wiederhold D L, Alexander D C, et al. *Coordinate gene activity in response to agents that induce systemic acquired resistance. Plant Cell* 1991, 3:1085-1094.

Wightwick A, Walters R, Allinson G, Reichman S, Menzies N: *Environmental Risks of Fungicides Used in Horticultural Production Systems. Fungicides* 2010, Odile Carisse (Ed.), ISBN: 978-953-307-266-1

Wilcox W F: *Grapevine Powdery Mildew*. Publication number 102GFSG-D2. New York State Integrated Pest Management Program, 2013

Winterhagen P, Howard S F, Qiu W, Kovacs L G: *Transcriptional Up-Regulation of Grapevine MLO Genesin Response to Powdery Mildew Infection. Am J Enol Vitic* 2008, 59:2

Zhao W, Fanning M L, Lane T: *Efficient RNAi-based gene family knockdown via set cover optimization. Artificial Intelligence in Medicine* 2005, 35, 61-73

Zheng Z, Nonomura T, Appiano M, Pavan S, Matsuda Y, Toyoda H, Wolters A A, Visser R G F1, Bai Y: *Loss of Function in Mlo Orthologs Reduces Susceptibility of Pepper and Tomato to Powdery Mildew Disease Caused by Leveillula taurica. PLOS One* 2013, 8(7):e70723

Zottini M, Barizza E, Costa A, Formentin E, Ruberti C, Carimi F, Lo Schiavo F: *Agroinfiltration of grapevine leaves for fast transient assays of gene expression and for long-term production of stable transformed cells. Plant Cell Rep* 2008, 27:845-853

---

What is claimed is:

1. An isolated *Vitis vinifera* comprising in its genome:
a first modification to a VvMLO6 gene encoding a protein having an amino acid sequence having at least 95% sequence identity to SEQ ID NO: 3, the modification to the VvMLO6 gene comprising one or more non-natural mutations, insertions, substitutions, or deletions, wherein the modification results in a reduction in expression of the protein having the amino acid sequence having at least 95% sequence identity to SEQ ID NO: 3 compared to a *Vitis vinifera* lacking said modification in said VvMLO6 gene encoding the protein having an amino acid sequence having at least 95% sequence identity to SEQ ID NO: 3; and
a second modification to a VvMLO11 gene encoding a protein having an amino acid sequence having at least 95% sequence identity to SEQ ID NO: 2, the modification to the VvMLO11 gene comprising one or more non-natural mutations, insertions, substitutions, or deletions, wherein the modification results in a reduction in expression of the protein having the amino acid sequence having at least 95% sequence identity to SEQ ID NO: 2 compared to a *Vitis vinifera* lacking said modification in said VvMLO11 gene encoding the protein having an amino acid sequence having at least 95% sequence identity to SEQ ID NO: 2,
wherein said *Vitis vinifera* having said modifications exhibits a reduction in powdery mildew disease severity compared to a *Vitis vinifera* lacking said modification modifications in said VvMLO6 gene and said VvMLO11 gene.

2. The isolated *Vitis vinifera* of claim 1, wherein the *Vitis vinifera* is a Long-Cluster Brachetto cultivar.

3. The isolated *Vitis vinifera* of claim 1, wherein the *Vitis vinifera* is a transgenic plant.

4. The isolated *Vitis vinifera* of claim 1, wherein the *Vitis vinifera* is a cultivated plant.

5. A seed, fruit, plant part, or propagation material of the isolated *Vitis vinifera* of claim 1, wherein the seed, fruit, plant part, or propagation material comprises the modified gene comprising one or more non-natural mutations, insertions, substitutions, or deletions resulting in:
   a decrease of function, loss of function, reduced expression, or absence of a protein having at least 95% sequence identity to SEQ ID NO: 3; and
   a decrease of function, loss of function, reduced expression, or absence of a protein having at least 95% sequence identity to SED ID NO: 2.

6. A method for obtaining a *Vitis vinifera* having resistance to powdery mildew comprising introducing a modification comprising one or more non-natural mutations, insertions, substitutions, or deletions to a VvMLO6 gene encoding a protein having at least 95% sequence identity to SEQ ID NO: 3 in a *Vitis vinifera*, wherein the modification results in:
   a decrease of function, loss of function, reduced expression, or absence of a protein having at least 95% sequence identity to SEQ ID NO: 3 compared to a *Vitis vinifera* lacking said modification in said VvMLO6 gene; and
introducing a second modification comprising one or more non-natural mutations, insertions, substitutions, or deletions to a VvMLO11 gene encoding a protein having at least 95% sequence identity to SEQ ID NO: 2 in a *Vitis vinifera*, wherein the second modification results in:
a decrease of function, loss of function, reduced expression, or absence of a protein having at least 95% sequence identity to SEQ ID NO: 2 compared to a *Vitis vinifera* lacking said modification in said VvMLO11 gene.

7. The method of claim 6, wherein the resistance to powdery mildew is resistance to powdery mildew caused by *Erysiphe necator*.

8. The method of claim 6, wherein the modified gene results in at least a 10% reduction in expression of the protein having at least 95% sequence identity to SEQ ID NO: 3 compared to a *Vitis vinifera* lacking said modification in said VvMLO6 gene.

* * * * *

UNITED STATES PATENT AND TRADEMARK OFFICE
CERTIFICATE OF CORRECTION

PATENT NO. : 11,441,157 B2
APPLICATION NO. : 16/887412
DATED : September 13, 2022
INVENTOR(S) : Mickael Malnoy et al.

It is certified that error appears in the above-identified patent and that said Letters Patent is hereby corrected as shown below:

On the Title Page

Column 2, Other Publications, Line 13, Delete "Occuring Borad-" and insert -- Occurring Board- --

Column 2, Other Publications, Line 28, Delete "Mio" and insert -- Mlo --

Column 2, Other Publications, Line 30, Delete "Unicinula" and insert -- Uncinula --

Column 2, Other Publications, Line 36, Delete "Confunction" and insert -- Cofunction --

In the Claims

Column 50, Lines 63-64, Claim 1, after "said" delete "modification"

Column 51, Line 15, Claim 5, delete "SED" and insert -- SEQ --

Signed and Sealed this
Twenty-second Day of November, 2022

Katherine Kelly Vidal
*Director of the United States Patent and Trademark Office*

SEQUENCE LISTING

```
<160> NUMBER OF SEQ ID NOS: 55

<210> SEQ ID NO 1
<211> LENGTH: 539
<212> TYPE: PRT
<213> ORGANISM: Vitis vinifera

<400> SEQUENCE: 1

Met Ala Asp Glu Leu Glu Glu Arg Ser Leu Glu Glu Thr Pro Thr Trp
1               5                   10                  15

Ala Val Ala Val Val Cys Phe Val Leu Leu Ala Val Ser Ile Phe Ile
            20                  25                  30

Glu His Ile Phe His Leu Ile Gly Ser Trp Leu Lys Gly Arg His Arg
        35                  40                  45

Arg Ala Leu Tyr Glu Ser Leu Glu Lys Ile Lys Ala Glu Leu Met Leu
    50                  55                  60

Leu Gly Val Ile Ser Leu Leu Leu Thr Ile Leu Gln Asp Tyr Ile Ser
65                  70                  75                  80

Lys Ile Cys Ile Ser Glu Ser Val Gly Ser Thr Trp His Pro Cys Lys
                85                  90                  95

Lys Glu Thr Lys Asp Phe Lys Asn Thr Cys Ser Glu Gly Lys Val Pro
            100                 105                 110

Leu Val Ser Ser Tyr Gly Ile His Gln Leu His Ile Phe Ile Phe Val
        115                 120                 125

Leu Ala Leu Phe His Val Ile Tyr Cys Val Ala Thr Leu Ala Leu Gly
    130                 135                 140

Arg Thr Lys Met Arg Arg Trp Lys Ala Trp Glu Asp Gln Thr Lys Thr
145                 150                 155                 160

Ile Glu Tyr Gln Tyr Ser His Asp Pro Glu Arg Phe Arg Phe Ala Arg
                165                 170                 175

Asp Thr Ser Phe Gly Arg Arg His Leu Asn Phe Trp Ser Arg Ser Pro
            180                 185                 190

Val Leu Leu Trp Ile Val Cys Phe Phe Arg Gln Phe Phe Arg Ser Val
        195                 200                 205

Asn Asn Val Asp Tyr Leu Thr Leu Arg His Gly Phe Ile Met Ala His
    210                 215                 220

Leu Ser Pro Gly Ser Glu Thr Lys Phe Asp Phe Arg Asn Tyr Ile Lys
225                 230                 235                 240
```

Arg Ser Leu Glu Glu Asp Phe Lys Val Val Ser Ile Ser Pro Val
            245                 250                 255

Ile Trp Phe Cys Ala Val Leu Phe Leu Thr Asn Thr His Gly Trp
            260                 265                 270

Tyr Ser Tyr Leu Trp Leu Pro Phe Ile Pro Leu Val Ile Ile Leu Leu
            275                 280                 285

Val Gly Thr Lys Leu Gln Val Ile Ile Thr Lys Leu Gly Leu Arg Ile
290                 295                 300

Ala Glu Arg Gly Asp Val Val Lys Gly Thr Pro Val Val Glu Pro Ala
305                 310                 315                 320

Asn Asp Leu Phe Trp Phe Asn Arg Pro His Leu Ile Leu Phe Leu Ile
            325                 330                 335

Asn Phe Val Leu Phe Leu Asn Ala Phe Gln Leu Ala Phe Phe Ala Trp
            340                 345                 350

Ser Thr Tyr Glu Phe Gly Leu Gln Ser Cys Tyr His Gln Lys Thr Glu
            355                 360                 365

Asp Ile Ala Ile Arg Ile Ser Met Gly Val Ile Thr Gln Val Leu Cys
            370                 375                 380

Ser Tyr Val Thr Leu Pro Leu Tyr Ala Leu Val Thr Gln Met Gly Ser
385                 390                 395                 400

Thr Met Arg Pro Thr Ile Phe Asn Glu Arg Val Ala Thr Ala Leu Arg
            405                 410                 415

Ser Trp His Gln Ala Ala Arg Lys His Thr Lys His Gly Arg His Ser
            420                 425                 430

Asn Gly Val Ser Pro Gln Ser Arg Pro Ala Thr Pro Ser Tyr Gly
            435                 440                 445

Met Ser Pro Val His Leu Leu Gln Gly Tyr His Asn His Thr Pro Asp
450                 455                 460

Met Ser Pro Arg Arg Ser Asn Leu Asp Asn Glu Trp Tyr Gly Glu Gly
465                 470                 475                 480

Ala Gly Ser Pro Gly Lys Lys Asp Asp Glu His Glu Lys Glu Lys
            485                 490                 495

Phe Glu Ser Arg Glu Gln Gly Gln Gly Ile Gly Asp Ser Ser Ser Thr
            500                 505                 510

Gln Leu Pro Leu Gly Pro Arg Pro Ile Arg Thr Gln His Glu Ile Asn
            515                 520                 525

Ile Thr Leu Ser Asp Phe Ser Phe Ala Lys Arg
            530                 535

<210> SEQ ID NO 2
<211> LENGTH: 583
<212> TYPE: PRT
<213> ORGANISM: Vitis vinifera

<400> SEQUENCE: 2

Met Ala Lys Gly Ser Lys Asp Arg Ser Leu Glu Gln Thr Pro Thr Trp
1               5                   10                  15

Ala Val Ala Val Val Cys Phe Val Leu Val Leu Ile Ser Ile Ile Ile
                20                  25                  30

Glu Tyr Ile Leu His Leu Ile Gly Lys Trp Leu Thr Lys Arg Asn Lys
                35                  40                  45

Arg Ala Leu Tyr Glu Ala Leu Glu Lys Ile Lys Ser Glu Leu Met Leu
            50                  55                  60

Leu Gly Phe Ile Ser Leu Leu Leu Thr Val Gly Gln Gly Thr Ile Ala

```
                65                  70                  75                  80
Gly Ile Cys Ile Ser Glu Lys Ile Ala Ala Thr Trp His Pro Cys Gly
                    85                  90                  95

Lys Lys Gln Glu Ile Lys Tyr Val Ser Asn Glu Glu Asp Tyr Gly Lys
                100                 105                 110

Arg Arg Leu Leu Glu Ile Ser Asp Ser Asp Gly Ser Asn Arg Arg Val
            115                 120                 125

Leu Ala Ala Ala Gly Asp Asp Lys Cys Gly Gly Lys Val Pro Phe
130                 135                 140

Val Ser Asn Tyr Gly Ile His Gln Leu His Ile Phe Ile Phe Val Leu
145                 150                 155                 160

Ala Val Phe His Val Leu Tyr Cys Ile Ile Thr Leu Ala Leu Gly Arg
                165                 170                 175

Ala Lys Met Arg Lys Trp Lys Ala Trp Glu Met Glu Thr Arg Thr Ala
                180                 185                 190

Glu Tyr Arg Phe Ala Asn Asp Pro Glu Arg Phe Arg Phe Ala Arg Asp
                195                 200                 205

Thr Ser Phe Gly Arg Arg His Leu His Ser Trp Ser Thr Ser Pro Val
            210                 215                 220

Leu Leu Trp Ile Val Cys Phe Phe Arg Gln Phe Val Arg Ser Val Pro
225                 230                 235                 240

Lys Val Asp Tyr Leu Thr Leu Arg His Gly Phe Ile Ile Ala His Leu
                245                 250                 255

Ala Pro Glu Ser His Thr Arg Phe Asp Phe Gln Lys Tyr Ile Lys Arg
                260                 265                 270

Ser Leu Glu Glu Asp Phe Lys Val Val Gly Ile Ser Pro Ile Ile
            275                 280                 285

Trp Phe Cys Ala Val Leu Phe Leu Leu Phe Asn Thr His Gly Trp His
                290                 295                 300

Ser Tyr Leu Trp Leu Pro Phe Ile Pro Leu Ile Ile Ile Leu Met Val
305                 310                 315                 320

Gly Thr Lys Leu Gln Val Ile Ile Thr Lys Met Gly Leu Arg Ile Gln
                325                 330                 335

Glu Arg Gly Glu Val Val Lys Gly Thr Pro Val Val Glu Pro Gly Asp
            340                 345                 350

Asp Leu Phe Trp Phe Asn Gln Pro Arg Leu Ile Leu Tyr Leu Ile Asn
            355                 360                 365

Phe Val Leu Phe Gln Asn Ala Phe Gln Val Ala Phe Phe Ala Trp Thr
370                 375                 380

Trp Tyr Glu Phe Gly Leu Lys Ser Cys Phe His Glu Arg Ile Glu Asp
385                 390                 395                 400

Val Val Ile Arg Ile Ser Met Gly Val Ile Val Gln Ile Leu Cys Ser
                405                 410                 415

Tyr Val Thr Leu Pro Leu Tyr Ala Leu Val Thr Gln Met Gly Ser Thr
                420                 425                 430

Met Lys Pro Thr Ile Phe Asn Asp Arg Val Ala Lys Ala Leu Arg Asn
                435                 440                 445

Trp His His Ala Ala Arg Lys His Ile Lys Gln Ser Lys Gln Ser Ser
                450                 455                 460

Ala Val Thr Pro Val Ser Ser Arg Ala Gly Thr Pro Phe Ser Ser Arg
465                 470                 475                 480

Pro Gly Thr Pro Leu His Gly Met Ser Pro Val His Leu Leu Arg His
                485                 490                 495
```

```
His Arg Ser Glu Leu Asp Ser Val Gln Thr Ser Pro Arg Met Ser Asn
            500                 505                 510

Phe Asp Asn Glu Gly Pro Glu Thr Asp Glu Tyr Arg His Arg Glu Asp
            515                 520                 525

Ile Ser Trp Ser Glu His His Arg Asn Pro Gly Pro Glu Glu Glu Gly
            530                 535                 540

Arg Asp Thr Asn His Arg Ile Leu Thr Arg Thr Met Pro Ala Pro Gln
545                 550                 555                 560

Ala Asp Asn Ala Gln His Glu Ile Asp Ile Gln Pro Met Asp Phe Ser
                565                 570                 575

Phe Asp Lys Arg Ala Arg Thr
            580

<210> SEQ ID NO 3
<211> LENGTH: 545
<212> TYPE: PRT
<213> ORGANISM: Vitis vinifera

<400> SEQUENCE: 3

Met Ala Asp Glu Leu Glu Asp Arg Ser Leu Thr Glu Thr Pro Thr Trp
1               5                   10                  15

Ala Val Ala Val Val Cys Phe Val Leu Leu Ala Val Ser Ile Phe Ile
            20                  25                  30

Glu His Ile Ile His His Ile Gly Ser Trp Leu Ala Arg Arg Asn Lys
        35                  40                  45

Arg Ala Leu Tyr Glu Ala Leu Glu Lys Ile Lys Ala Glu Leu Met Leu
    50                  55                  60

Leu Gly Phe Met Ser Leu Leu Thr Val Leu Gln Thr Pro Ile Ser
65                  70                  75                  80

Lys Ile Cys Ile Ser Lys Ser Val Gly Ser Thr Trp Tyr Pro Cys Asp
                85                  90                  95

Val Asp Glu Lys Glu Phe Lys Asn Thr Cys Gly Thr Glu Ser Gly Lys
            100                 105                 110

Val Pro Phe Val Ser Tyr Tyr Gly Ile His Gln Leu His Ile Phe Ile
            115                 120                 125

Phe Val Leu Ala Leu Phe His Val Ile Tyr Cys Val Ala Thr Leu Ala
        130                 135                 140

Leu Gly Thr Tyr Lys Met Arg Arg Trp Lys Thr Trp Glu Asp Glu Thr
145                 150                 155                 160

Arg Thr Ala Glu Tyr Gln Tyr Ser His Asp Pro Glu Arg Phe Arg Tyr
                165                 170                 175

Ala Arg Glu Thr Ser Phe Gly Arg Arg His Leu Asn Phe Trp Ser Ser
            180                 185                 190

Ser Pro Val Leu Leu Trp Ile Val Cys Phe Phe Arg Gln Phe Tyr Gly
        195                 200                 205

Ser Val His Arg Asp Asp Tyr Leu Ala Leu Arg His Gly Phe Ile Val
    210                 215                 220

Ala His Leu Ala Pro Glu Ser Glu Arg Lys Phe Asp Phe Arg Lys Tyr
225                 230                 235                 240

Ile His Arg Ser Leu Glu Glu Asp Phe Lys Ala Val Val Gly Ile Ser
                245                 250                 255

Pro Val Ile Trp Phe Cys Ala Ile Leu Phe Leu Leu Thr Asn Thr His
            260                 265                 270

Gly Trp Tyr Ser Tyr Phe Trp Leu Pro Phe Ile Pro Leu Ile Ile Leu
```

```
                   275                 280                 285
Leu Leu Val Gly Thr Lys Leu Gln Val Ile Ile Thr Glu Leu Gly Leu
    290                 295                 300
Arg Ile Ala Glu Arg Gly Val Val Lys Gly Thr Pro Ile Val Glu
305                 310                 315                 320
Pro Gly Asp His Leu Phe Trp Phe Asn Arg Pro Ser Leu Met Leu Phe
                325                 330                 335
Leu Ile Asn Phe Val Leu Phe Leu Asn Ala Phe Gln Leu Ala Phe Phe
            340                 345                 350
Ala Trp Ser Thr Tyr Gly Leu Lys Ser Cys Tyr His Asp Thr Thr Glu
        355                 360                 365
Asp Tyr Val Ile Arg Ile Thr Met Gly Val Met Thr Gln Val Leu Cys
    370                 375                 380
Ser Tyr Val Thr Leu Pro Leu Tyr Ala Leu Val Thr Gln Met Gly Thr
385                 390                 395                 400
Thr Met Arg Ser Thr Val Phe Asn Asp Lys Val Ala Val Ala Leu Arg
                405                 410                 415
Asp Trp His Glu Thr Ala Arg Lys His Thr Arg His Gly His Ser Asp
            420                 425                 430
Gly Val Ser Pro Gln Ser Ser Arg Pro Ser Thr Pro Ser Tyr Gly Met
        435                 440                 445
Ser Pro Val His Leu Leu Gln Ser Tyr Asp Asn Asn Thr Pro Asp Met
    450                 455                 460
Ser Pro Val Ala Ser Asn Tyr Asp Asn Glu Arg Trp Tyr Gly Glu Gly
465                 470                 475                 480
Ser Gly Ser Leu Gly Lys Lys Asp Asp Glu Gln Arg Pro Glu Asn
                485                 490                 495
Phe Glu Ser Arg Glu Pro Gly Arg Gly Thr Gln Asp Ser Ser Ala
            500                 505                 510
Gln Leu Ala Leu Gly Pro Leu Pro Ile Gln Thr Gln His Glu Val Asn
        515                 520                 525
Ile Thr Ser Ser Glu Phe Ser Phe Arg Arg Ser Pro Arg Ser Pro Arg
    530                 535                 540
Pro
545

<210> SEQ ID NO 4
<211> LENGTH: 1620
<212> TYPE: DNA
<213> ORGANISM: Vitis vinifera

<400> SEQUENCE: 4
atggctgatg aacttgaaga gcgtagtttg gaggaaacgc ctacttgggc tgttgcagtg      60
gtctgctttg tgttgcttgc tgtttcgatc ttcatcgaac atattttca tcttattgga     120 tcgtggttaa aaggcagaca caggcgagcc ctttatgaat ctctggaaaa gatcaaagca     180
gagcttatgc tgttgggagt catatccttg ctgcttacaa tattacaaga ttacatttca     240
aagatatgca tttctgagag tgttgggtcc acttggcacc ttgtaaaaa ggaaaccaaa      300 gattttaaga cacatgctc tgagggaaaa gtcccattag tgtcttccta tgggatccat     360
caactccata tattcatctt tgtgttagct ctctttcatg tgatttactg tgtggccacc     420
ttggctttgg gaagaaccaa gatgagaaga tggaaggctt gggaggatca aactaagacg     480
attgaatatc aatactctca tgatccagag aggtttaggt ttgcaaggga tacatccttt     540
```

```
gggcgcaggc atttgaattt ctggagccgc tctcctgttc tcctctggat tgtctgcttc      600
ttcagacaat tcttcagatc ggttaacaac gttgactatc ttacattaag acatggattt      660
atcatggcac atttgtcacc tggaagtgaa acaaaatttg atttccgaaa ttacatcaaa      720
agatcgcttg aagaggactt caaagttgta gtgagcatca gcccagtaat atggttctgt      780
gcagtattgt tcctactcac caacacacat gggtggtatt cttacttgtg cttccattc       840 atccccttag ttataatact cttggtggga acaaagcttc aagtgatcat aaccaaactg      900
ggattgagga ttgcagagag aggtgatgtg gtgaagggta caccagtagt tgagccagcc      960
aacgacctct tctggttcaa tcgccctcac ctcatcctct ttctgatcaa ctttgttctc     1020
ttcctgaatg catttcagct ggcttttcttc gcatggagca cgtatgagtt tgggctgcaa    1080
tcttgctatc accaaaagac agaagacatt gccatcagaa tctcaatggg ggtcatcaca     1140
caggtactat gcagttatgt gacactccca ctctatgcct tggtgacaca gatgggctcc     1200
accatgagac cgacaatttt taacgagaga gtggccacgg ctctaagaag ctggcaccag     1260
gcggccagga agcacacaaa acatgggcgc cactcgaatg tgtgtccccc acagtcgagt     1320
aggccagcga ctccatcata tgggatgtcc cctgttcatc tattgcaagg ctaccacaac     1380
cacactcctg atatgtctcc aagacgatca aacttggaca cgaatggta tggggaagga     1440 gcagggtctc cagggaagaa ggatgatgat gagcatgaaa aggagaaatt tgaatccaga     1500
gagcagggac aagggattgg agactcgagc tcaacccaac tgccccttgg accccgccca     1560
atccgaaccc aacatgagat caacattact ttatcggatt tctcatttgc aaagcgctga     1620

<210> SEQ ID NO 5
<211> LENGTH: 2063
<212> TYPE: DNA
<213> ORGANISM: Vitis vinifera

<400> SEQUENCE: 5
atggctaagg gatcaaagga tcgatctttg gagcaaacac cgacttgggc ggttgcagtg       60
gtctgttttg tgctggtttt gatatcaatt atcatcgaat acatccttca cttaattgga      120
aagtggctaa caaagagaaa caaacgagct ctttatgaag cacttgaaaa gattaagtca      180
gaacttatgc tactggggtt catatcgctg ctcctaacgg taggacaagg aactattgcg      240
ggatatgcat atcagagaa gattgcagca acctggcacc catgtgggaa gaaacaagaa      300
atcaagtatg tttctaatga agaagattat ggcaagagaa ggcttcttga atttcagat       360 tccgatggaa gtaatcgacg tgtgttagcg gccgcgggag atgacaaatg tggagagggt      420
aaagtcccgt ttgtctccaa ttatgggatc caccaacttc acatattcat cttcgttctt      480
gctgttttcc acgtacttta ttgtataatc acattggctt tgggcagagc taagatgagg      540
aagtggaagg cgtgggaaat ggaaacaaga acagccgagt accggttcgc aaacgatcca      600
gagagattta ggtttgcaag agacacctca tttgggagaa ggcatttgca ctcctggagc      660
acctccccag ttctcctttg gattgtgtgt tcttcagac aatttgtcag atcagttccc      720
aaagttgatt acttgaccct gcgccatggg tttatcattg cacatttggc acccgagagt      780
catactagat ttgatttcca gaaatacatc aagagatcac tcgaggagga tttcaaagtt      840
gtagtcggta tcagtccaat aatctggttc tgtgctgtac tcttcctact attcaacacc      900
catggttggc attcttatct atggttaccc tttatcccac taattatcat cctgatggtg      960
gggacaaaac tacaagttat cataacaaag atggggctga aatacagga gagaggagag     1020 gtggtaaaag gaaccccagt ggtggagcct ggtgatgatc ttttctggtt caaccagcca     1080
```

```
cgtctcattc tctacctgat taactttgtt ctctttcaga acgcattcca ggttgccttc   1140
tttgcatgga cctggtatga gtttggcttg aaatcttgtt tccacgaaag gatagaagat   1200
gtggtcatcc gcatatcaat gggagtcata gtacaaatac tctgcagcta tgtgactctt   1260
cctctgtatg ccttggttac acagatggga tctaccatga gcccaccat cttcaatgac    1320 agagtggcga aagctctgag aaactggcac cacgctgcaa ggaagcacat aaaacagagc   1380
aagcaatcaa cgcgctgtga ccctgtatca agtagggcag gcactccctt ttcaagtagg   1440
ccaggcaccc ccttacatgg catgtccct gttcatctac tccgccacca ccgcagtgag    1500
ctcgacagtg ttcaaacatc tcctagaatg tccaattttg acaatgaagg tccggagaca   1560
gacgagtatc gccaccgtga ggatatatca tggtcagaac atcatagaaa tcctggtcca   1620
gaagaagagg ggagggacac aaatcatagg atcttgaccc gtaccatgcc agctcctcaa   1680
gctgacaatg ctcagcacga aattgacatt cagcccatgg acttttcatt cgataaaaga   1740
gcaagaactt gaatagagtg atgaagattg gattgaggaa gcaaagatga caacaaaacc   1800
catccctggt tgtatagtgg atacaatgtt gaacttgcac cttggccttg tattttttt    1860 tttttttgagg atcactcgta tagctgtggg caacgaattt ttctgaaaag taactcttgt   1920
agttctgtaa gttttaaatt tcgttgtacc gtatatcata aattgtgagc agtcaaattc   1980
ttacatgagt tctcgtgtaa gaatcaacta aatgcccaaa atcaagccaa tgctttcccc   2040
aaaaaaaaaa aaaaaaaaaa aaa                                           2063

<210> SEQ ID NO 6
<211> LENGTH: 1790
<212> TYPE: DNA
<213> ORGANISM: Vitis vinifera

<400> SEQUENCE: 6
atggctgatg aacttgaaga tcgtagtttg acggaaacgc ctacttgggc tgttgcagtg     60
gtctgttttg tgttgcttgc tgtttcgatc ttcatcgaac atattattca tcatattgga    120
tcgtggttag caagaagaaa caagcgagcc ctttatgaag ctctggaaaa gatcaaagca    180
gagcttatgc tgttgggatt catgtccttg ctgcttacag tattacaaac tcccatttca    240
aagatatgca tttctaagag tgttggatcc acttggtacc cttgtgatgt tgatgagaaa    300
gaatttaaaa acacatgcgg cactgaatca ggaaaagtcc catttgtgtc ttactatggg    360
atccatcagc tccatatatt tatctttgtg ctagctctct ttcatgtgat ctactgcgtg    420
gccaccttgg ctttgggaac atacaagatg agaagatgga agacttggga ggatgaaact    480
aggacagctg aatatcaata ctctcatgat ccagagaggt ttaggtatgc aagggaaaca    540
tcctttgggc gcaggcattt gaatttctgg agcagctctc ctgttctcct atggattgtg    600
tgcttcttta gacaattcta cggatcggtt cacagagatg actatcttgc tttaagacat    660
ggatttatcg tggcacattt ggcacccgaa agcgaaagaa aatttgattt ccggaagtac    720
atccacagat cacttgaaga ggacttcaaa gctgtagtgg gcatcagccc agtaatatgg    780
ttctgtgcaa tattgttcct actcaccaac acacatgggt ggtattctta cttttggctt    840
ccattcatcc ccttaattat actgctcttg gtgggaacaa agctacaagt gataataacc    900
gaattgggat tgaggattgc agagagaggt gttgtggtga agggtacacc aatagttgaa    960
ccaggcgacc acctcttttg gttcaatcgc cccagcctca tgctctttct gatcaacttc   1020
gttctctttc tgaatgcatt tcagctggct ttctttgcat ggagcacgta tgggttgaaa   1080
```

```
tcttgctatc atgacactac tgaagattat gtcatcagaa tcacaatggg ggtcatgaca      1140
caggtactgt gcagttatgt gacactccca ctctatgcct tagtgacaca gatgggcacc      1200
accatgagat cgactgtttt taatgacaaa gtagccgtgg ctctaagaga ctggcacgag      1260
acggccagaa agcacactag acacgggcac tcggatggtg tgtccccaca gtcaagtagg      1320
ccatcgaccc catcatatgg gatgtcccca gttcatctgt tgcaaagcta cgacaacaac      1380
actcctgata tgtctccagt ggcatcaaac tacgacaacg aacggtggta tggagaagga      1440
tcagggtctc tagggaagaa ggatgatgat gagcaaaggc cagagaattt tgaatcgaga      1500
gagccgggac gagggactca agactcaagc tcagcccaat tggccctggg acccctcccc      1560
attcaaactc aacatgaggt caacatcact tcatcagagt tctcatttcg taggagccca      1620
aggagcccaa ggccatgact tcgatgatgc gaaggatgat taattgagga caaaactccg      1680
cgtattgatt tggtattttg tttttcgttt ctgcagtttg tattttgcat gtacatttgt      1740 taccccttgta attcgatcaa tttatgtttc ttcaaaaaaa aaaaaaaaa                1790
```

```
<210> SEQ ID NO 7
<211> LENGTH: 20
<212> TYPE: DNA
<213> ORGANISM: Artificial Sequence
<220> FEATURE:
<223> OTHER INFORMATION: EF1alpha forward primer

<400> SEQUENCE: 7
gaactgggtg cttgataggc                                                   20

<210> SEQ ID NO 8
<211> LENGTH: 24
<212> TYPE: DNA
<213> ORGANISM: Artificial Sequence
<220> FEATURE:
<223> OTHER INFORMATION: EF1alpha reverse primer

<400> SEQUENCE: 8
aaccaaaata tccggagtaa aaga                                              24

<210> SEQ ID NO 9
<211> LENGTH: 21
<212> TYPE: DNA
<213> ORGANISM: Artificial Sequence
<220> FEATURE:
<223> OTHER INFORMATION: GAPDH forward primer

<400> SEQUENCE: 9
ttctcgttga gggctattcc a                                                 21

<210> SEQ ID NO 10
<211> LENGTH: 21
<212> TYPE: DNA
<213> ORGANISM: Artificial Sequence
<220> FEATURE:
<223> OTHER INFORMATION: GAPDH reverse primer

<400> SEQUENCE: 10
ccacagactt catcggtgac a                                                 21

<210> SEQ ID NO 11
<211> LENGTH: 21
<212> TYPE: DNA
<213> ORGANISM: Artificial Sequence
<220> FEATURE:
<223> OTHER INFORMATION: Actin forward primer
```

<400> SEQUENCE: 11
tccttgcctt gcgtcatcta t                                              21

<210> SEQ ID NO 12
<211> LENGTH: 23
<212> TYPE: DNA
<213> ORGANISM: Artificial Sequence
<220> FEATURE:
<223> OTHER INFORMATION: Actin reverse primer

<400> SEQUENCE: 12
caccaatcac tctcctgcta caa                                            23

<210> SEQ ID NO 13
<211> LENGTH: 21
<212> TYPE: DNA
<213> ORGANISM: Artificial Sequence
<220> FEATURE:
<223> OTHER INFORMATION: VvMLO6 forward primer

<400> SEQUENCE: 13
gtgcagttat gtgacactcc c                                              21

<210> SEQ ID NO 14
<211> LENGTH: 17
<212> TYPE: DNA
<213> ORGANISM: Artificial Sequence
<220> FEATURE:
<223> OTHER INFORMATION: VvMLO6 reverse primer

<400> SEQUENCE: 14
acacaccatc cgagtgc                                                   17

<210> SEQ ID NO 15
<211> LENGTH: 20
<212> TYPE: DNA
<213> ORGANISM: Artificial Sequence
<220> FEATURE:
<223> OTHER INFORMATION: VvMLO7 forward primer

<400> SEQUENCE: 15
ctttcttcgc atggagcacg                                                20

<210> SEQ ID NO 16
<211> LENGTH: 20
<212> TYPE: DNA
<213> ORGANISM: Artificial Sequence
<220> FEATURE:
<223> OTHER INFORMATION: VvMLO7 reverse primer

<400> SEQUENCE: 16
gagcccatct gtgtcaccaa                                                20

<210> SEQ ID NO 17
<211> LENGTH: 17
<212> TYPE: DNA
<213> ORGANISM: Artificial Sequence
<220> FEATURE:
<223> OTHER INFORMATION: VvMLO11 forward primer

<400> SEQUENCE: 17 gcacccctt acatggc                                                    17

<210> SEQ ID NO 18

```
<211> LENGTH: 23
<212> TYPE: DNA
<213> ORGANISM: Artificial Sequence
<220> FEATURE:
<223> OTHER INFORMATION: VvMLO11 reverse primer

<400> SEQUENCE: 18
tctggaccag gatttctatg atg                                              23

<210> SEQ ID NO 19
<211> LENGTH: 20
<212> TYPE: DNA
<213> ORGANISM: Artificial Sequence
<220> FEATURE:
<223> OTHER INFORMATION: VvMLO13 forward primer

<400> SEQUENCE: 19
ctggtgacac agatgggttc                                                  20

<210> SEQ ID NO 20
<211> LENGTH: 20
<212> TYPE: DNA
<213> ORGANISM: Artificial Sequence
<220> FEATURE:
<223> OTHER INFORMATION: VvMLO13 reverse primer

<400> SEQUENCE: 20
ctacttgaca tgggtgtggc                                                  20

<210> SEQ ID NO 21
<211> LENGTH: 20
<212> TYPE: DNA
<213> ORGANISM: Artificial Sequence
<220> FEATURE:
<223> OTHER INFORMATION: VvWRKY19 forward primer

<400> SEQUENCE: 21
ggggaggctg tggttaggtt                                                  20

<210> SEQ ID NO 22
<211> LENGTH: 20
<212> TYPE: DNA
<213> ORGANISM: Artificial Sequence
<220> FEATURE:
<223> OTHER INFORMATION: VvWRKY19 reverse primer

<400> SEQUENCE: 22
gtttggcatt tggcttgtct                                                  20

<210> SEQ ID NO 23
<211> LENGTH: 22
<212> TYPE: DNA
<213> ORGANISM: Artificial Sequence
<220> FEATURE:
<223> OTHER INFORMATION: VvWRKY27 forward primer

<400> SEQUENCE: 23
cttggatcag aatcacccct aa                                               22

<210> SEQ ID NO 24
<211> LENGTH: 21
<212> TYPE: DNA
<213> ORGANISM: Artificial Sequence
<220> FEATURE:
<223> OTHER INFORMATION: VvWRKY27 reverse primer

<400> SEQUENCE: 24
```

```
gccgtggtat gtggttttgt a                                              21

<210> SEQ ID NO 25
<211> LENGTH: 22
<212> TYPE: DNA
<213> ORGANISM: Artificial Sequence
<220> FEATURE:
<223> OTHER INFORMATION: VvWRKY48 forward primer

<400> SEQUENCE: 25
caagatttca aggaccaagc ag                                             22

<210> SEQ ID NO 26
<211> LENGTH: 21
<212> TYPE: DNA
<213> ORGANISM: Artificial Sequence
<220> FEATURE:
<223> OTHER INFORMATION: VvWRKY48 reverse primer

<400> SEQUENCE: 26
agtatgcctt cctcggtatg t                                              21

<210> SEQ ID NO 27
<211> LENGTH: 22
<212> TYPE: DNA
<213> ORGANISM: Artificial Sequence
<220> FEATURE:
<223> OTHER INFORMATION: VvWRKY52 forward primer

<400> SEQUENCE: 27
cctcttgatg atgggtttag tt                                             22

<210> SEQ ID NO 28
<211> LENGTH: 21
<212> TYPE: DNA
<213> ORGANISM: Artificial Sequence
<220> FEATURE:
<223> OTHER INFORMATION: VvWRKY52 reverse primer

<400> SEQUENCE: 28
gtcttccacg gtaggtgatt t                                              21

<210> SEQ ID NO 29
<211> LENGTH: 26
<212> TYPE: DNA
<213> ORGANISM: Artificial Sequence
<220> FEATURE:
<223> OTHER INFORMATION: VvEDS1 forward primer

<400> SEQUENCE: 29
agggttttat attgttatct caaggc                                         26

<210> SEQ ID NO 30
<211> LENGTH: 33
<212> TYPE: DNA
<213> ORGANISM: Artificial Sequence
<220> FEATURE:
<223> OTHER INFORMATION: VvEDS1 reverse primer

<400> SEQUENCE: 30
ggaagaaaat atcttattac tacataatgt ttc                                 33

<210> SEQ ID NO 31
<211> LENGTH: 20
<212> TYPE: DNA
```

```
<213> ORGANISM: Artificial Sequence
<220> FEATURE:
<223> OTHER INFORMATION: VvLOX9 forward primer

<400> SEQUENCE: 31
gacaagaagg acgagccttg                                               20

<210> SEQ ID NO 32
<211> LENGTH: 20
<212> TYPE: DNA
<213> ORGANISM: Artificial Sequence
<220> FEATURE:
<223> OTHER INFORMATION: VvLOX9 reverse primer

<400> SEQUENCE: 32
cataagggta ctgcccgaaa                                               20

<210> SEQ ID NO 33
<211> LENGTH: 20
<212> TYPE: DNA
<213> ORGANISM: Artificial Sequence
<220> FEATURE:
<223> OTHER INFORMATION: VvLOX1 forward primer

<400> SEQUENCE: 33
atcaatgctc ttgctcggga                                               20

<210> SEQ ID NO 34
<211> LENGTH: 20
<212> TYPE: DNA
<213> ORGANISM: Artificial Sequence
<220> FEATURE:
<223> OTHER INFORMATION: VvLOX1 reverse primer

<400> SEQUENCE: 34
ccagagctgg tcataggcag                                               20

<210> SEQ ID NO 35
<211> LENGTH: 20
<212> TYPE: DNA
<213> ORGANISM: Artificial Sequence
<220> FEATURE:
<223> OTHER INFORMATION: VvPAD4 forward primer

<400> SEQUENCE: 35
acgattgcac tggtaagcca                                               20

<210> SEQ ID NO 36
<211> LENGTH: 20
<212> TYPE: DNA
<213> ORGANISM: Artificial Sequence
<220> FEATURE:
<223> OTHER INFORMATION: VvPAD4 reverse primer

<400> SEQUENCE: 36
cgactccgtc atcgcctaaa                                               20

<210> SEQ ID NO 37
<211> LENGTH: 20
<212> TYPE: DNA
<213> ORGANISM: Artificial Sequence
<220> FEATURE:
<223> OTHER INFORMATION: VvPEN1 forward primer

<400> SEQUENCE: 37
cttcgcaaga agctcaggga                                               20
```

<210> SEQ ID NO 38
<211> LENGTH: 20
<212> TYPE: DNA
<213> ORGANISM: Artificial Sequence
<220> FEATURE:
<223> OTHER INFORMATION: VvPEN1 reverse primer

<400> SEQUENCE: 38
tgctcttgga tcgccttctg                                              20

<210> SEQ ID NO 39
<211> LENGTH: 20
<212> TYPE: DNA
<213> ORGANISM: Artificial Sequence
<220> FEATURE:
<223> OTHER INFORMATION: VvPR1 forward primer

<400> SEQUENCE: 39
cccagaactc tccacaggac                                              20

<210> SEQ ID NO 40
<211> LENGTH: 20
<212> TYPE: DNA
<213> ORGANISM: Artificial Sequence
<220> FEATURE:
<223> OTHER INFORMATION: VvPR1 reverse primer

<400> SEQUENCE: 40
gcagctacag tgtcgttcca                                              20

<210> SEQ ID NO 41
<211> LENGTH: 20
<212> TYPE: DNA
<213> ORGANISM: Artificial Sequence
<220> FEATURE:
<223> OTHER INFORMATION: VvPR6 forward primer

<400> SEQUENCE: 41
acgaaaacgg catcgtaatc                                              20

<210> SEQ ID NO 42
<211> LENGTH: 20
<212> TYPE: DNA
<213> ORGANISM: Artificial Sequence
<220> FEATURE:
<223> OTHER INFORMATION: VvPR6 reverse primer

<400> SEQUENCE: 42
tcttactggg gcaccatttc                                              20

<210> SEQ ID NO 43
<211> LENGTH: 20
<212> TYPE: DNA
<213> ORGANISM: Artificial Sequence
<220> FEATURE:
<223> OTHER INFORMATION: VvNPF3.2 forward primer

<400> SEQUENCE: 43
tcgtcacatc agcacagctt                                              20

<210> SEQ ID NO 44
<211> LENGTH: 20
<212> TYPE: DNA
<213> ORGANISM: Artificial Sequence
<220> FEATURE:

<223> OTHER INFORMATION: VvNPF3.2 reverse primer

<400> SEQUENCE: 44
atctgcgagc caatggaaca                                               20

<210> SEQ ID NO 45
<211> LENGTH: 20
<212> TYPE: DNA
<213> ORGANISM: Artificial Sequence
<220> FEATURE:
<223> OTHER INFORMATION: 35S promoter

<400> SEQUENCE: 45
cgcacaatcc cactatcctt                                               20

<210> SEQ ID NO 46
<211> LENGTH: 27
<212> TYPE: DNA
<213> ORGANISM: Artificial Sequence
<220> FEATURE:
<223> OTHER INFORMATION: VvMLO6 forward primer

<400> SEQUENCE: 46
cacctgctta cagtattaca aactccc                                       27

<210> SEQ ID NO 47
<211> LENGTH: 20
<212> TYPE: DNA
<213> ORGANISM: Artificial Sequence
<220> FEATURE:
<223> OTHER INFORMATION: VvMLO6 reverse primer

<400> SEQUENCE: 47
tttcccttgc atacctaaac                                               20

<210> SEQ ID NO 48
<211> LENGTH: 25
<212> TYPE: DNA
<213> ORGANISM: Artificial Sequence
<220> FEATURE:
<223> OTHER INFORMATION: VvMLO7 forward primer

<400> SEQUENCE: 48
caccgacaat ttttaacgag agagt                                         25

<210> SEQ ID NO 49
<211> LENGTH: 21
<212> TYPE: DNA
<213> ORGANISM: Artificial Sequence
<220> FEATURE:
<223> OTHER INFORMATION: VvMLO7 reverse primer

<400> SEQUENCE: 49
atctcatgtt gggttcggat t                                             21

<210> SEQ ID NO 50
<211> LENGTH: 24
<212> TYPE: DNA
<213> ORGANISM: Artificial Sequence
<220> FEATURE:
<223> OTHER INFORMATION: VvMLO11 forward primer

<400> SEQUENCE: 50
cacctcactt atgctactgg ggtt                                          24

```
<210> SEQ ID NO 51
<211> LENGTH: 24
<212> TYPE: DNA
<213> ORGANISM: Artificial Sequence
<220> FEATURE:
<223> OTHER INFORMATION: VvMLO11 reverse primer

<400> SEQUENCE: 51
atcaactttg ggaactgatc tgac                                              24

<210> SEQ ID NO 52
<211> LENGTH: 24
<212> TYPE: DNA
<213> ORGANISM: Artificial Sequence
<220> FEATURE:
<223> OTHER INFORMATION: VvMLO13 forward primer

<400> SEQUENCE: 52
caccgagcta atgttgctag ggtt                                              24

<210> SEQ ID NO 53
<211> LENGTH: 20
<212> TYPE: DNA
<213> ORGANISM: Artificial Sequence
<220> FEATURE:
<223> OTHER INFORMATION: VvMLO13 reverse primer

<400> SEQUENCE: 53
aaattttgca tggctttgag                                                   20

<210> SEQ ID NO 54
<211> LENGTH: 20
<212> TYPE: DNA
<213> ORGANISM: Artificial Sequence
<220> FEATURE:
<223> OTHER INFORMATION: VvALS1 forward primer

<400> SEQUENCE: 54
ccgtgcatac cgagcatttg                                                   20

<210> SEQ ID NO 55
<211> LENGTH: 20
<212> TYPE: DNA
<213> ORGANISM: Artificial Sequence
<220> FEATURE:
<223> OTHER INFORMATION: VvALS1 reverse primer

<400> SEQUENCE: 55
aggccggttc tgtatgttgg                                                   20
```